US011944568B2

(12) United States Patent
Oh

(10) Patent No.: US 11,944,568 B2
(45) Date of Patent: *Apr. 2, 2024

(54) COOLING SYSTEM FOR LOCALIZED AND NON-INVASIVE COOLING TREATMENT

(71) Applicant: DIVERGENT MED LLC, Beverly Hills, CA (US)

(72) Inventor: Sung Oh, West Covina, CA (US)

(73) Assignee: DIVERGENT MED LLC, Beverly Hills, CA (US)

( * ) Notice: Subject to any disclaimer, the term of this patent is extended or adjusted under 35 U.S.C. 154(b) by 920 days.

This patent is subject to a terminal disclaimer.

(21) Appl. No.: 16/939,050

(22) Filed: Jul. 26, 2020

(65) Prior Publication Data

US 2020/0360176 A1    Nov. 19, 2020

Related U.S. Application Data

(63) Continuation of application No. 15/510,968, filed as application No. PCT/US2015/049436 on Sep. 10, 2015, now Pat. No. 10,758,404.

(60) Provisional application No. 62/050,653, filed on Sep. 15, 2014.

(51) Int. Cl.
*A61F 7/00* (2006.01)
*A61F 7/02* (2006.01)

(52) U.S. Cl.
CPC ...... *A61F 7/007* (2013.01); *A61F 2007/0075* (2013.01); *A61F 2007/0078* (2013.01); *A61F 2007/0093* (2013.01); *A61F 2007/0239* (2013.01); *A61F 2007/029* (2013.01)

(58) Field of Classification Search
CPC .............. A61F 7/007; A61F 2007/0075; A61F 2007/02
See application file for complete search history.

(56) References Cited

U.S. PATENT DOCUMENTS

| 3,132,688 A | 5/1964 | Nowak |
| 3,950,789 A | 4/1976 | Konz et al. |
| 4,338,944 A | 7/1982 | Arkans |
| 4,470,263 A | 9/1984 | Lehovec et al. |

(Continued)

FOREIGN PATENT DOCUMENTS

| WO | WO 2009095639 A2 | 8/2009 |
| WO | WO 2013074664 A1 | 5/2013 |

OTHER PUBLICATIONS

International Preliminary Examination Report dated Mar. 21, 2017 from corresponding PCT Application No. PCT/US2015/049436.

(Continued)

*Primary Examiner* — Kaitlyn E Smith
(74) *Attorney, Agent, or Firm* — Henricks Slavin LLP

(57) ABSTRACT

The cooling system (100, 300, 400, 500, 700, 750) includes an applicator (101, 501, 701) configured to hold a predetermined amount of solid coolant and fluid coolant (117) to cool a targeted area of the body (162, 570) to crystalize the lipid-rich cells underneath the targeted area to reduce the fat cells. The applicator may include a thermoelectric cooler (TEC, 136, 704, 706) where the hot side is cooled by coolant held within the applicator. The cold side of the TEC may be thermally coupled to a cooling plate (138, 560) configured to cool a targeted area of the skin at a predetermined temperature range for a predetermined period of time. The cooling system may also be used to relieve localized pain at certain area of the body and/or utilized for cryotherapy.

18 Claims, 28 Drawing Sheets

(56) References Cited

U.S. PATENT DOCUMENTS

| | | |
|---|---|---|
| 4,741,338 A | 5/1988 | Miyamae |
| 4,790,369 A | 12/1988 | Avrea |
| 4,930,317 A | 6/1990 | Klein |
| 4,962,761 A | 10/1990 | Golden |
| 5,097,829 A | 3/1992 | Quisenberry |
| 5,137,530 A | 8/1992 | Sand |
| 5,561,981 A | 10/1996 | Quisenberry et al. |
| 5,755,753 A | 5/1998 | Knowlton |
| 5,800,490 A | 9/1998 | Patz et al. |
| 5,871,526 A | 2/1999 | Gibbs et al. |
| 5,961,475 A | 10/1999 | Guitay |
| 6,017,337 A | 1/2000 | Pira |
| 6,104,959 A | 8/2000 | Spertell |
| 6,273,884 B1 | 8/2001 | Altshuler et al. |
| 6,311,090 B1 | 10/2001 | Knowlton |
| 6,350,276 B1 | 2/2002 | Knowlton |
| 6,430,446 B1 | 8/2002 | Knowlton |
| 6,500,141 B1 | 12/2002 | Irion et al. |
| 6,567,696 B2 | 5/2003 | Voznesensky et al. |
| 6,662,054 B2 | 12/2003 | Kreindel et al. |
| 6,840,955 B2 | 1/2005 | Ein |
| 6,846,322 B2 | 1/2005 | Kane et al. |
| 7,217,265 B2 | 5/2007 | Hennings et al. |
| 7,276,058 B2 | 10/2007 | Altshuler et al. |
| 7,367,341 B2 | 5/2008 | Anderson et al. |
| 7,854,754 B2 | 12/2010 | Ting et al. |
| 8,192,474 B2 | 6/2012 | Levinson |
| 8,275,442 B2 | 9/2012 | Allison |
| 8,285,390 B2 | 10/2012 | Levinson et al. |
| 8,337,539 B2 | 12/2012 | Ting et al. |
| 8,603,073 B2 | 5/2013 | Allison |
| 8,523,927 B2 | 9/2013 | Levinson et al. |
| 8,676,338 B2 | 3/2014 | Levinson |
| 8,702,774 B2 | 4/2014 | Baker et al. |
| 8,834,547 B2 | 9/2014 | Anderson et al. |
| 9,132,031 B2 | 9/2015 | Levinson et al. |
| 9,134,368 B2 | 9/2015 | Kuo et al. |
| 9,375,345 B2 | 6/2016 | Levinson et al. |
| 9,408,745 B2 | 8/2016 | Levinson et al. |
| 9,545,523 B2 | 1/2017 | Nanda |
| 9,844,460 B2 | 12/2017 | Weber et al. |
| 9,844,461 B2 | 12/2017 | Levinson et al. |
| 2003/0220674 A1 | 11/2003 | Anderson et al. |
| 2008/0077211 A1 | 3/2008 | Levinson et al. |
| 2008/0287839 A1 | 11/2008 | Rosen et al. |
| 2009/0312823 A1 | 12/2009 | Patience et al. |
| 2010/0280582 A1 | 11/2010 | Baker et al. |
| 2011/0009847 A1 | 1/2011 | Levinson et al. |
| 2011/0060322 A1 | 3/2011 | Manstein |
| 2011/0224683 A1 | 9/2011 | Manstein |
| 2011/0238050 A1 | 9/2011 | Allison et al. |
| 2011/0238051 A1 | 9/2011 | Levinson et al. |
| 2011/0300079 A1 | 12/2011 | Martens et al. |
| 2012/0022518 A1 | 1/2012 | Levinson |
| 2012/0227927 A1 | 9/2012 | Fujiya et al. |
| 2013/0079684 A1 | 3/2013 | Rosen et al. |
| 2013/0158636 A1 | 6/2013 | Ting et al. |
| 2013/0253384 A1 | 9/2013 | Anderson et al. |
| 2013/0253494 A1 | 9/2013 | Anderson et al. |
| 2014/0005760 A1 | 1/2014 | Levinson et al. |
| 2014/0364841 A1 | 12/2014 | Kornstein |
| 2016/0051401 A1 | 2/2016 | Yee et al. |

OTHER PUBLICATIONS

Bernstein et al., "Non-Invasive Fat Reduction of the Flanks Using a New Cyrolipolysis Applicator and Overlapping, Two-Cycle Treatments," Laser in Surgery and Medicine 46:731-735 (2014).

Krueger, et al., "Cryolipolysis for noninvasive body contouring: clinical efficacy and patient satisfaction," Clinical, Cosmetic and Investigational Dermatology 2014:7 201-205.

Sasaki et al., "Noninvasive Selective Cryolipolysis and Reperfusion Recovery for Localized Natural Fat Reduction and Contouring," Aesthetic Surgery Journal 2014, vol. 34(3) 420-411.

Stevens, "Does Cryolipolysis Lead to Skin Tightening? A First Report of Cryodermadstringo," Aesthetic Surgery Journal 2014, vol. 34(6) NP32-NP34.

Stevens et al., "Cryolipolysis Conformable-Surface Applicator for Nonsurgical Fat Reduction in Lateral Thighs," Aesthetic Surgery Journal 2015, vol. 35(1) 66-71.

Zelickson et al., "Cryolipolysis for Safe and Effective Inner Thigh Fat Reduction," Lasers in Surgery and Medicine 47:120-127 (2015).

US 11,944,568 B2

COOLING SYSTEM FOR LOCALIZED AND NON-INVASIVE COOLING TREATMENT

CROSS-REFERENCE TO RELATED APPLICATIONS

The present Application is a continuation of U.S. application Ser. No. 15/510,968, filed Mar. 13, 2017, which is a U.S. national phase application under 35 U.S.C. § 371 of International Patent Application No. PCT/US2015/049436, filed Sep. 10, 2015, which claims the benefit of U.S. Provisional Patent Application Ser. No. 62/050,653, filed Sep. 15, 2014. The entire disclosures of both the PCT and Provisional Applications are incorporated herein by reference.

FIELD

This invention is directed a cooling system that cools a targeted lipid-rich cells; and in particular, to a cooling system that cools the targeted lipid-rich cells at a predetermined range of temperatures for a predetermined period of time to crystallize the lipid-rich cells due to the cooling effects.

BACKGROUND

Cryotherapy is a local or general use of low temperatures, generally exposing the body to subzero (0° C.) temperatures, for health benefits. Cryotherapy has been used to decrease inflammation, increase cellular survival, decrease pain and spasms, and promote overall health. It is not generally considered as a medical procedure, but a non-invasive option for people seeking relief from pain and faster recovery from injuries. The application of extreme cold temperature has also been used to destroy abnormal or diseased tissue. Cryotherapy has also been used to treat a number of diseases and disorders, such as warts, moles, skin tags, solar keratosis, and to treat inflammation due to gout.

Cryotherapy has also been used to cool targeted lipid-rich cells, such as excess body fat, to crystallize the lipid-rich cells to reduce the fat cells. Once the targeted fat cells are crystallized, the crystallized fat cells may die and the immune system of the body naturally eliminates the crystallized fat cells from the body. This results in a localized reduction of fat in the treated area part of the body such that the user can target the area where he or she wants to reduce the fat cell and look better. One of the advantages of the cooling method for removing fatty tissue is that it does not require surgery or significant recovery time. However, cooling methods such as the methods described in U.S. Pat. No. 7,367,341, which is hereby incorporated by reference, and other cryotherapies require complicated machinery, such as a pump to circulate coolant fluid to the cooling applicator to maintain the cooling temperature at a desired level. Having complicated machinery such as a pump and an electronic cooling control system can add costs and complexity to the applicator such that many potential users may not be able to afford the cooling procedure and/or cryotherapy. As such, there is a need for a cooling system that can lower the temperature, such as below subzero (0° C.) temperatures, around a targeted area of the body for health benefits such as crystallizing the targeted fat cells to reduce the fat cells in the targeted area of body/skin, without the complicated pump to make the cooling control system simple to use and more affordable.

INVENTION SUMMARY

A cooling system is configured to be placed over a targeted area of the skin and cool the targeted area of the skin at a predetermined cool temperature range for a predetermined period of time to crystalize a portion of the fat cells underneath the targeted area of the skin in order to reduce the fat cells underneath the targeted area of the skin. The cooling system may also be applied over the targeted area of the skin to relieve pain and/or for cryotherapy. The cooling system includes an applicator configured to hold a predetermined amount of coolant. The applicator may include a thermoelectric cooler (TEC) having a hot side and a cold side. The coolant can be poured into the container or contained within the applicator. The coolant may be thermally couple to the hot side of the TEC to draw the heat away from the hot side to control the temperature of the cold side of the TEC. The hot side may be thermally coupled to a radiator to improve the efficiency of drawing heat away from the hot side. The cold side may be thermally coupled to a cooling plate configured to cool a targeted area of the skin at a predetermined temperature range for a predetermined period of time.

One aspect of the invention is directed to a cooling system for extracting heat away from a targeted area of the body, the cooling system comprising: a thermoelectric cooler (TEC) having a first side and a second side; and an applicator configured to hold a predetermined amount of coolant, the applicator housing the TEC so that when the applicator is filled with the predetermined amount of the coolant the first side of the TEC is thermally coupled to the coolant, and the applicator having a cooling side thermally coupled to the second side of the TEC and configured to extract heat away from the targeted area of the body.

Another aspect of the invention is directed to a cooling system including an applicator having a thermoelectric cooler (TEC) with a hot side and a cold side, the applicator configured to hold coolant thermally coupled to the hot side of the TEC such that the cold side can lower the temperature of a targeted area of the skin at a predetermined cool temperature range for a predetermined period of time, the applicator having a sensor to detect whether the coolant is an authorized coolant, the cooling system including: a predetermined amount of coolant including an antifreeze ingredient and an authentication ingredient to maintain the predetermined amount of coolant fluid below −5° C., and the authentication ingredient detectable by the senor to determine if the predetermined amount of coolant is an authorized coolant.

Yet another aspect of the invention is directed to a method of cooling a targeted area of the skin, the method comprising: chilling a predetermined amount of coolant; holding the predetermined amount of coolant within an applicator having at least one thermoelectric cooler (TEC) having a hot side and a cold side; placing the applicator over the targeted area of the skin; conducting heat away from the hot side to the predetermined amount of coolant held within the applicator; and controlling the temperature of the cold side of the TEC to cool the targeted area of the skin within a predetermined range of cool temperatures for a predetermined period time.

Still another aspect of the invention is directed to a cooling system configured to cool a targeted area of the skin, the cooling system including: a predetermined amount of coolant capable of being chilled below −5° C. and remain substantially fluid; an applicator having a thermoelectric cooler (TEC) with a hot side and a cold side, the applicator configured to receive the predetermined amount of coolant such that the hot side of the TEC is thermally coupled to the predetermined amount of coolant and the cold side of the TEC configured to cool the targeted area of the skin; and a power supply to provide power to the TEC to cool the cold side of the TEC.

Another aspect of the invention is directed to a method of cooling a targeted area of the skin with an applicator having a thermoelectric cooler (TEC) with a hot side and a cold side, the hot side thermally coupled to a predetermined amount of coolant within the applicator to cool the hot side to maintain the cold side at a predetermined range of temperatures for a predetermined period of time, the method comprising: measuring the temperature of the predetermined amount of coolant within the applicator; calculating a rate of temperature increase of the predetermined amount of coolant; and adjusting the temperature of the cold side of the TEC to an upper temperature limit within the predetermined range of temperatures if the rate of temperature increase is too high so that the temperature of the cold side of the TEC is within the predetermined temperature range for the predetermined period of time.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE INVENTION

Figure 1:
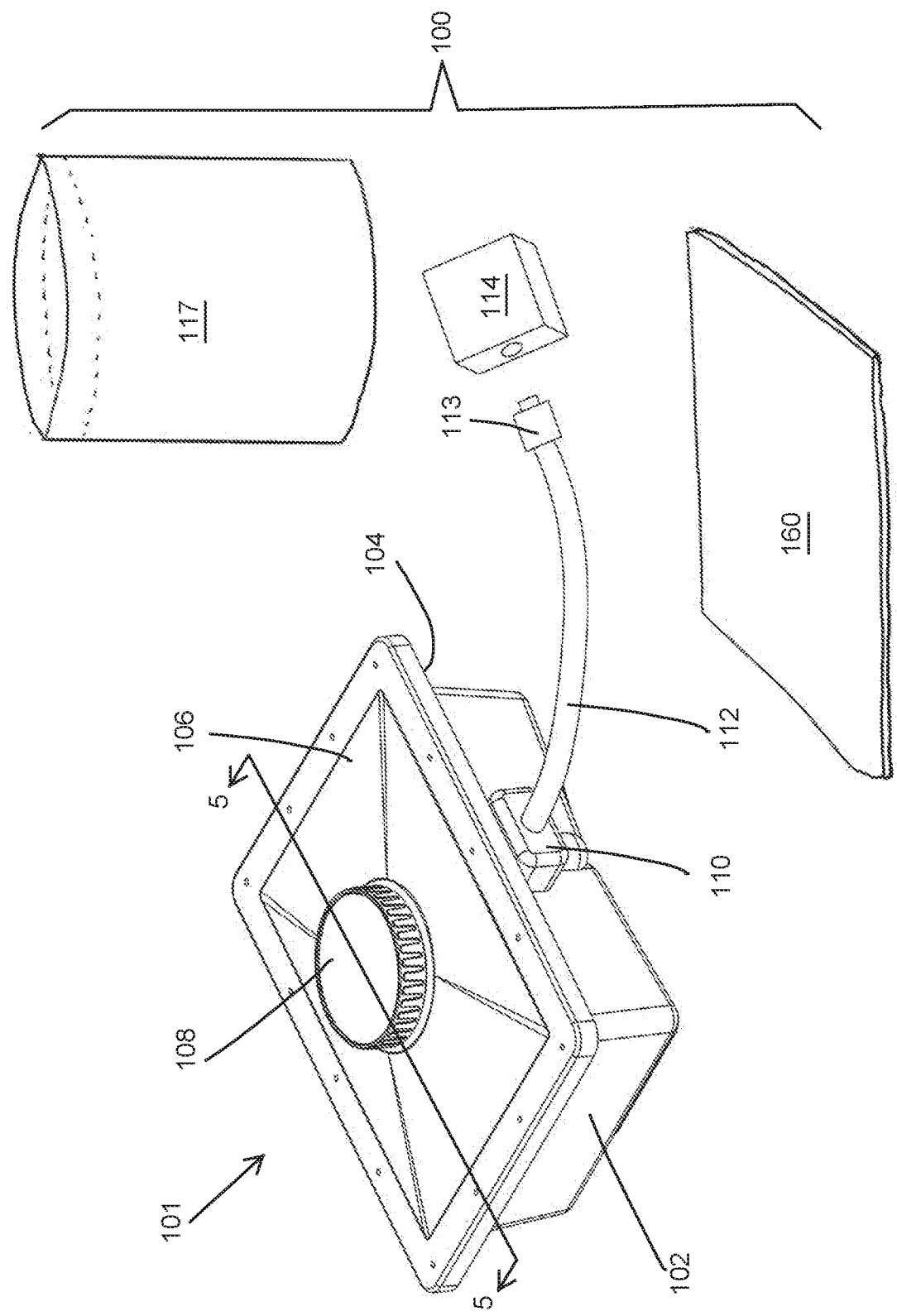
FIG. 1 shows a perspective of a cooling system.

FIG. 1 shows a perspective of a cooling system 100 including an applicator 101, a power supply 114, a pouch 117 fill with fluid coolant, and an antifreeze liner 160. The applicator 101 may have a container 102 with a rim 104 adapted to couple to a lid 106. The lid 106 may have a cover 108 adapted to release from the lid 106. For example, the cover 108 may be rotated either clockwise or counter-clockwise direction to tighten onto the lid or released from the cover 108, respectively. As discussed in more details below, the applicator 101 may include a thermoelectric cooler (not shown in FIG. 1, referred to as TEC) with a hot side and a cold side to cool a targeted area of the skin within a predetermined range of temperatures for a predetermined period of time. The applicator 101 may have a duct 110 to route the electrical cables 112 from the TEC that terminates into a plug 113 that is adapted to electrically couple to a power supply 114. The lid 106 may be coupled to the container 102 in a variety of ways. For instance, the lid 106 may be coupled to the container 102 through nuts and bolts such that coolant inside the applicator may be substantially sealed therewithin such that the coolant does not leak. Alternatively, the lid 106 may be hinged to the container 102 such that the lid may open and close along one edge similar to a lid on an ice box.

The cooling system 100 may include a pouch 117 with fluid coolant inside. As discussed in more detail below, the coolant may include an antifreeze ingredient that keep the coolant fluid below 0° C. or at lower temperatures such as −5° C., −10° C., and −15° C. In preparation for the cooling procedure, the pouch may be placed inside a freezer until the temperature of the coolant inside the pouch 117 reach a steady state temperature, such as more than 12 hours. With the cover 108 opened, the coolant may be poured into the applicator 101 to cool the hot side of the TEC, and power to the TEC may be adjusted accordingly to control the temperature of the cold side of the TEC within the desired temperature range to chill the fat cell underneath the targeted area of the skin. The cooling system 100 may also include the antifreeze liner 160 which may be placed over the targeted area of the skin to protect the skin from freeze damage. Once the liner 160 is placed over the targeted area of the skin, the applicator may be placed over the liner 160 for the cooling procedure.

Figure 2:
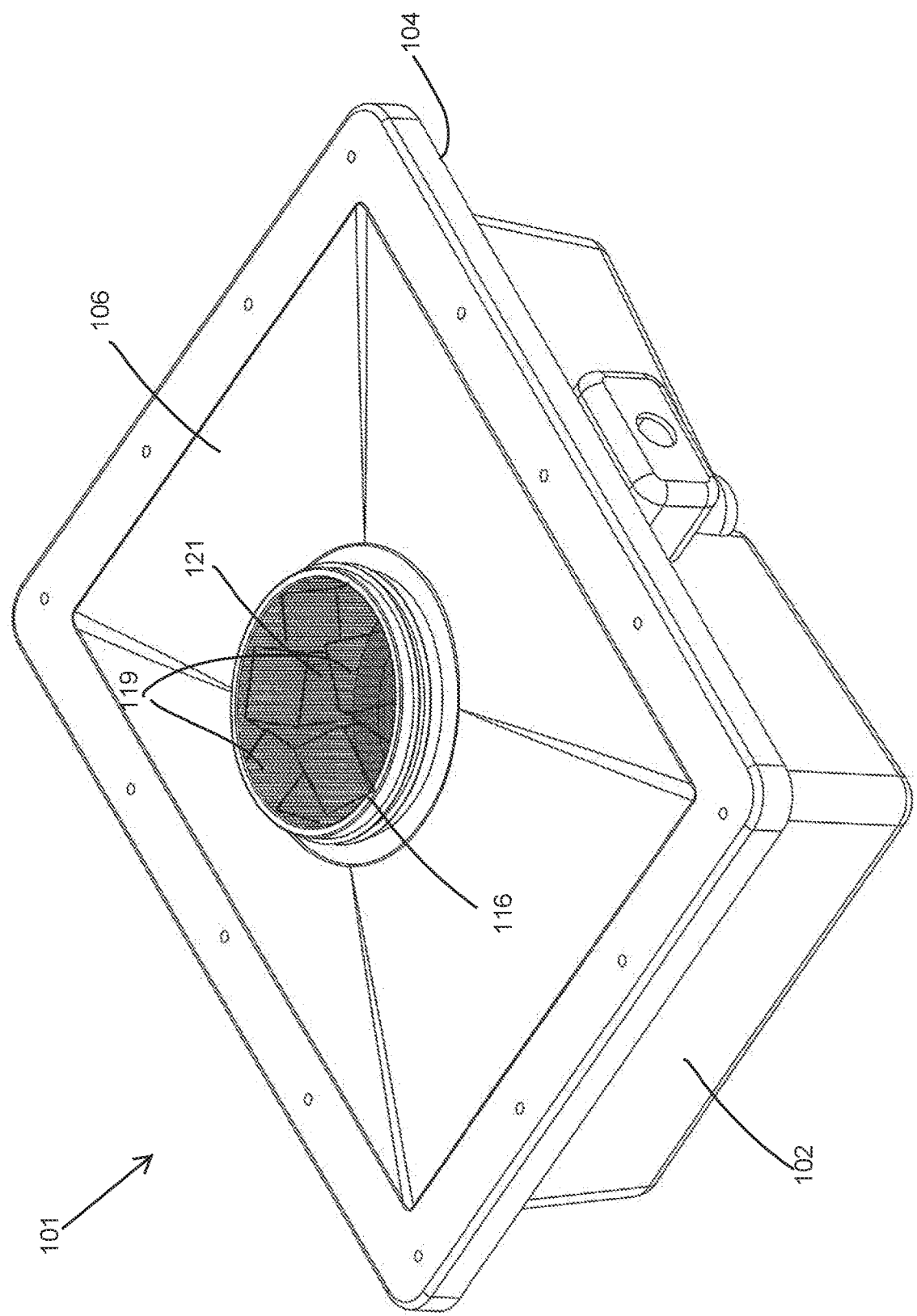
FIG. 2 shows the applicator with the cover removed showing a first portion of solid coolant and a second portion of fluid coolant.

FIG. 2 shows the applicator 101 with the cover 108 removed, which exposes an opening 116 of the lid 106. With the cover 108 removed, coolant may be placed inside the applicator 101. The coolant may include a first portion of solid coolant and a second portion of fluid coolant. The first portion of the solid coolant may be ice cubes 119, which may be first inserted into the container until the applicator is substantially full of ice cubes. The second portion of the fluid coolant 121 may be poured into the applicator to fill the gaps among the ice cube 119 until the fluid coolant substantially fill the applicator 101. The fluid coolant 121 inside the pouch 117 may be chilled below −5° C. before being poured into the applicator 101. The container 102 may be formed from a flexible non-porous material such as rubber or any other material known to one skilled in the art configured to hold coolant therewithin and flexible to contour the shape of the targeted area of the body. The applicator may be configured to hold from 60 oz to 140 oz of coolant; and in particular, from 80 oz to 120 oz of coolant, and in further particular about 100 oz of coolant. It should be noted, the size of the applicator is not limited to any particular volume range noted above. Rather, the size of the applicator may be determined by the cooling application such that the applicator may be sized and configured to hold sufficient amount of coolant to cool the targeted area of the skin within a predetermined range of temperatures for a predetermined amount of time. In general, lower the required cooling temperature of the targeted area of the skin or a longer period of cooling procedure, a larger applicator 101 may be required to hold more coolant. In other words, more coolant may be needed to conduct the heat away from the hot side of the TEC so that the cold side of the TEC may be cooled to a lower temperature or for a longer period of treatment time.

Figure 3:
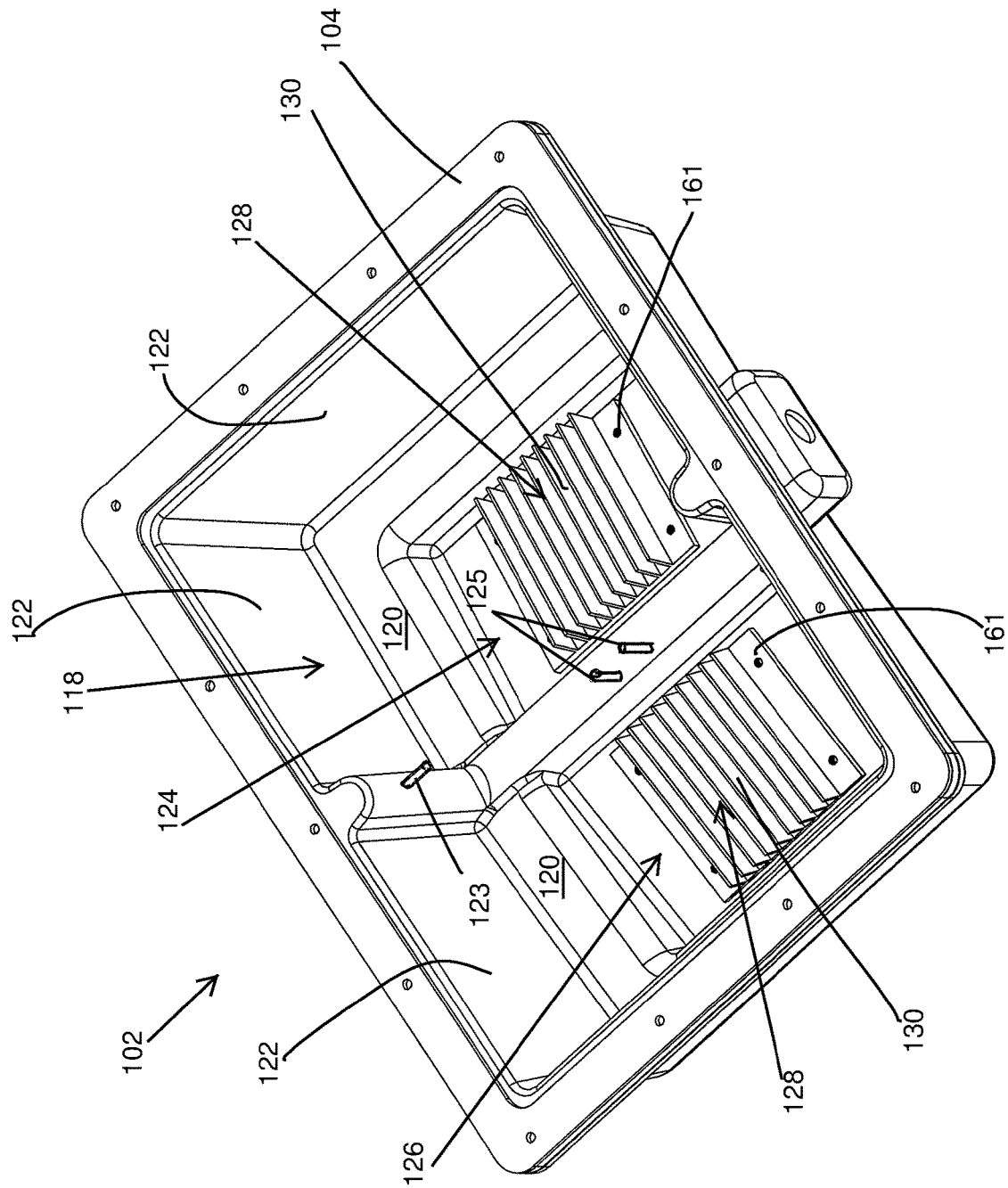
FIG. 3 shows the applicator with the lid removed showing the interior space of the applicator.

FIG. 3 shows the applicator 101 with the lid 106 removed showing the interior space 118 of the container 102. The container 102 may have a base 120 with side walls 122 extending upward and forming the rim 104. The base 120 of the container 102 may form first and second pods 124 and 126, and each pod may be adapted to couple to a thermoelectric cooling system 128 (TEC system). The TEC system 128 may include a radiator 130 which may be cooled by the first portion of the solid coolant and the second portion of the fluid coolant within the container 102 as discussed in more detail below. The applicator 101 may also include a temperature sensor 123 to measure the temperature of the coolant inside the container 102. The container 102 may also include sensors 125 to measure certain properties of the coolant such as its electrical conductivity, salt level, and etc. in order to identify the coolant as being an authorized coolant, if the coolant is within a certain parameter so that the coolant works properly with the applicator.

Figure 4:
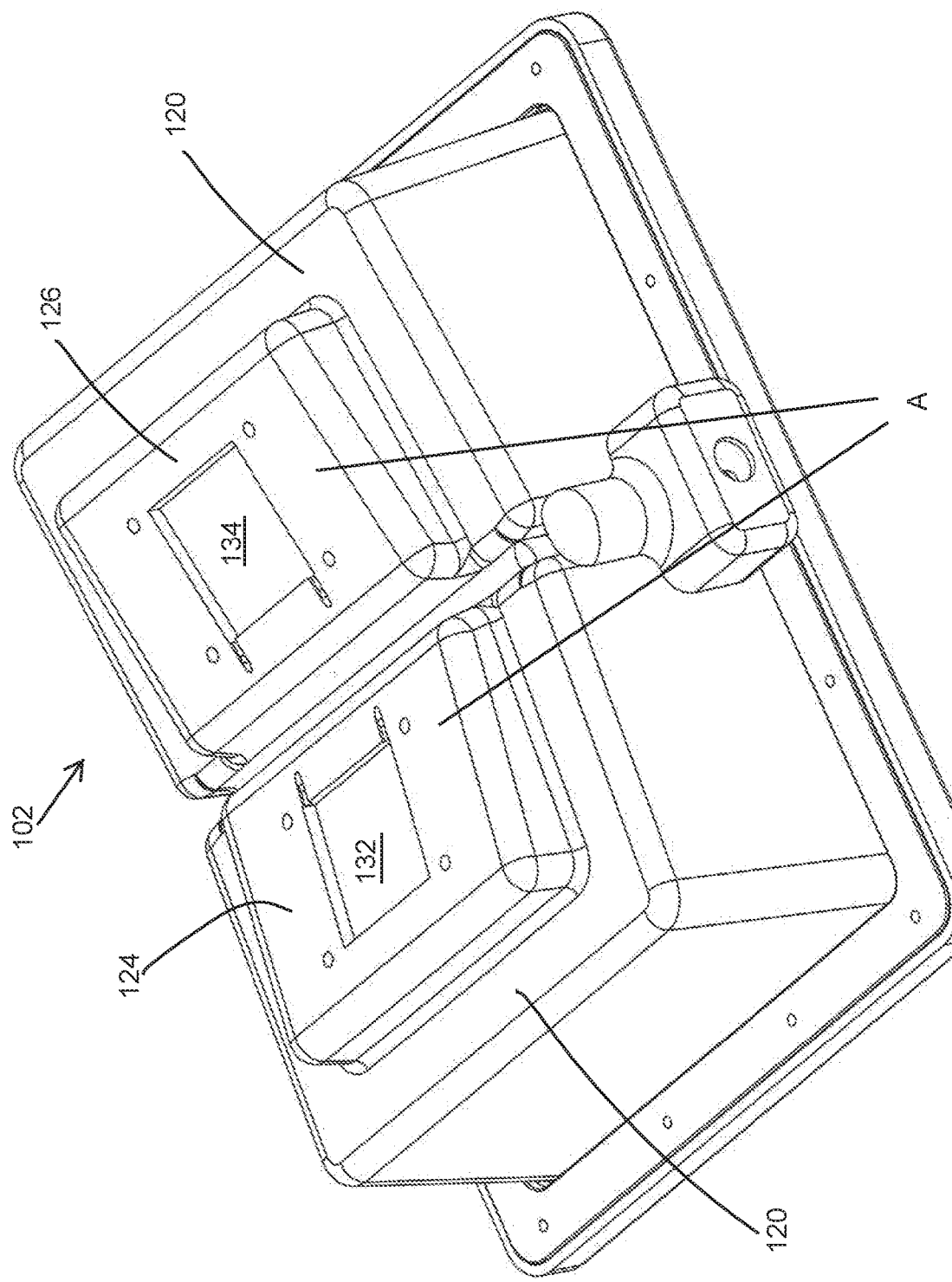
FIG. 4 shows an underside of the applicator.

FIG. 4 shows an underside of the container 102 having the base 120 with the first and second pods 124 and 126 protruding therefrom. The first and second pods may have their respective cutouts 132 and 134, adapted to receive a TEC (not shown) and a corresponding cooling plate (not shown) discussed in more detail below. The planer surfaces of the first and second pods 124 and 126 may be at an obtuse angle "A" or be less than 180° relative to each other so that the two pods 124 and 126 may contour the outer shape of the targeted area of the body to better improve the surface area contact between the cooling plates (not shown) and the targeted area of the skin.

Figure 5:
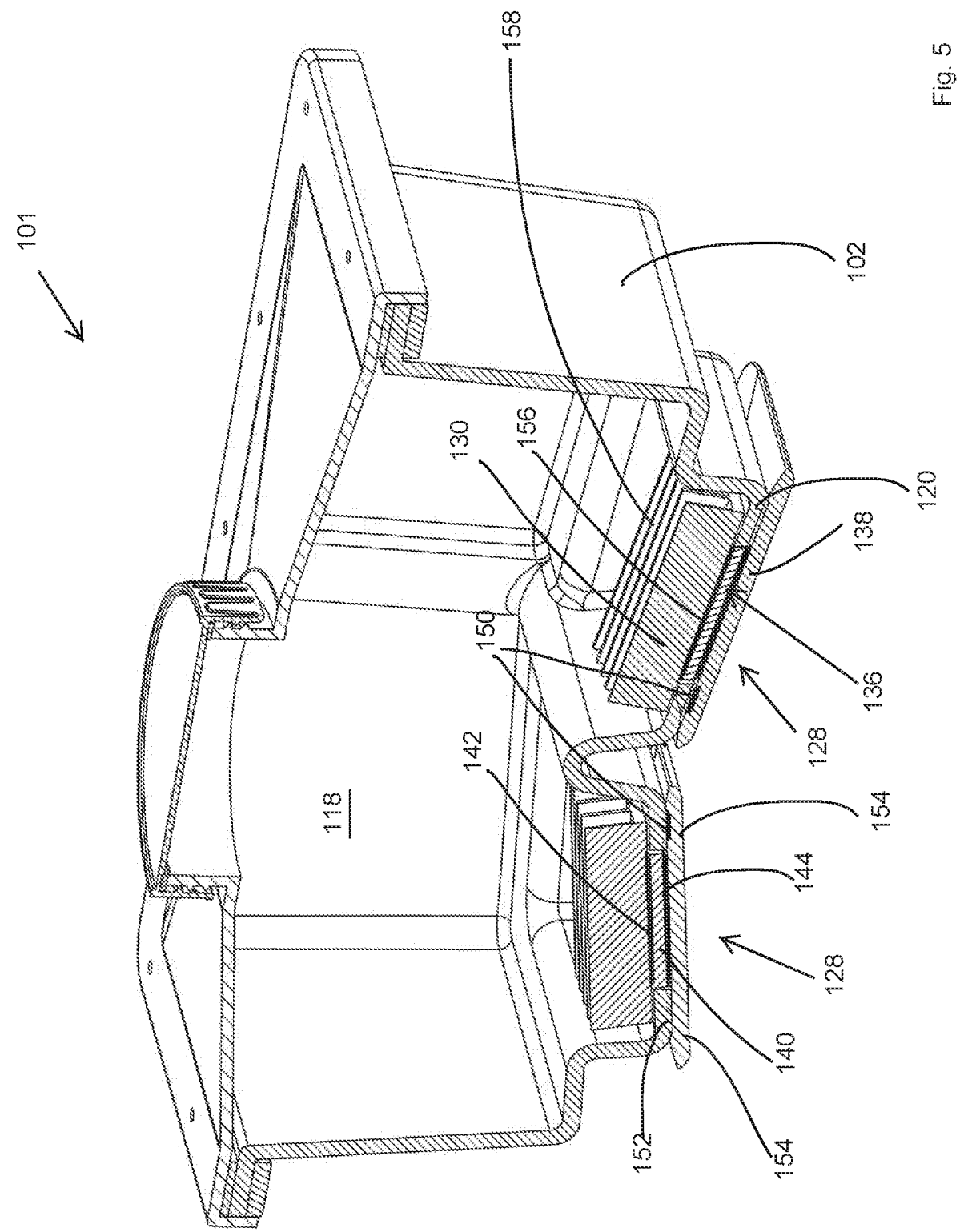
FIG. 5 shows a cross-sectional view of the applicator along the line 5-5 shown in FIG. 1.

FIG. 5 shows a cross-sectional view of the applicator 101 along the line 5-5 shown in FIG. 1. The TEC system 128 may include a TEC 136 between the radiator 130 and a cooling plate 138. The TEC 136 has an intermediate layer 140 between a first side 142 and a second side 144. The power to the TEC 136 may be provided such that the first side 142 may be the hot side and the second side 144 may be the cold side. The TEC 136 may utilize the Peltier effect where whenever direct current passes through the circuit of heterogeneous conductors, heat is either released or absorbed at the conductors' junctions, which depends on the current polarity. The amount of heat may be proportional to the current that passes through conductors. When direct current moves across a Peltier device, it causes temperature differential between the first and second sides 142 and 144. As a result, the first side 142 may be hot while the opposite second side 144 may be cold or cooler relative to the first side 142, and vice versa if the polarity of direct current is reversed. In general, if the heat generated on the hot side is effectively dissipated into heat sinks and further into the surrounding environment, then the temperature on the cold side may be much lower than that of the ambient by dozens of degrees. The TEC's cooling capacity may be proportional to the current passing through the interconnected layer 140.

The applicator 101 may also include one or more temperature sensors 150 adapted to measure the temperature of the cooling plate 138 to estimate the temperature of the targeted area of the skin of the user. The temperature along the cooling plate 138 may be maintained within a predetermined range of temperatures by adjusting the power supplied to the TEC 136. For instance, if the temperature sensor 150 indicates that the temperature of the cooling plate 138 is below a predetermined lower limit cooling temperature, the power to the TEC 136 may be reduced or turned OFF such that the temperature of the second side 144 may rise, and vice versa. The radiators 130 may be thermally coupled to the first side 142 of the TEC to dissipate the heat more efficiently using a thermal paste for example. Conversely, if the temperature sensor 150 indicates that the temperature of the cooling plate is above the predetermined cooling upper limit temperature, then the power to the TEC may be increased or turned ON or the polarity of the voltage may be reversed so that the temperature of the second side 144 may be lowered. This way, the temperature of the treated area of the skin may be substantially maintained within a predetermined range of temperatures.

The cooling plate 138 may be formed from a thermally conductive material such as aluminum, copper, iron, stainless steel, and thermally conductive plastic. The cooling plate 138 may have a first side 152 and a second side 154. The cooling plates may also be formed from 3D printing process to customize the shape of the cooling plate for surface areas of the body parts that have sharp bends such as chin and foot areas. For instance, a cooling system with a customized cooling plate for user's chin may be used to remove fatty cells within the chin area. The base 156 of the radiator 130 may overlap the cutout 132 adapted to substantially seal the cutout 132 such that liquid and/or coolant may be substantially prevented from leaking through the gaps between the TEC 136 and the cutout 132. Thermal paste may be applied between the base 156 and the first side 142 of the TEC 136, and between the second side 144 of the TEC 136 and the first side 152 of the cooling plate to improve the efficiency of conducting heat through the radiator 130, TEC 136, and the cooling plate 138.

A gasket and/or sealant may be also applied between the base 120 of the container 102 and the base 156 of the radiator to substantially prevent liquid from leaking through the gap between the TEC 136 and the cutout 132. The radiator 130 may have a plurality of fins 158 to improve the efficiency of dissipating heat away from the TEC 136. Couplers 161 (see FIG. 3) such as rivets, screws, anchors, and the like may be used to couple the radiator 130 and the cooling plate 138 together so that the radiator, TEC, and the cooling plate may substantially maintain thermal contact with each other. The lid 106 may be releasably sealed to the rim 104 of the container 102 to substantially prevent coolant within the container from leaking and substantially preventing atmospheric air from entering the container.

The internal space 118 of the container 102 may be sized to hold sufficient amount of the first portion of the solid coolant such as ice cubes alone and/or in combination with the second portion of the fluid coolant to substantially maintain the cooling plate 138 temperature within a predetermined range of temperatures, such as from about −15° C. to about 10° C., and in more particularly from about −10° C. to about 0° C. or from about −6° C. to about −4° C. for about 20 minutes to about 120 minutes, from about 60 minutes to about 120 minutes, and from about 75 minutes to about 90 minutes. Each of the cooling plates 138 may have a temperature sensor 150 to monitor the temperature between the cooling plates and the targeted area of the skin to maintain the temperature at a predetermined range by controlling the voltage and/or current provided to the TEC 136.

Figure 6:
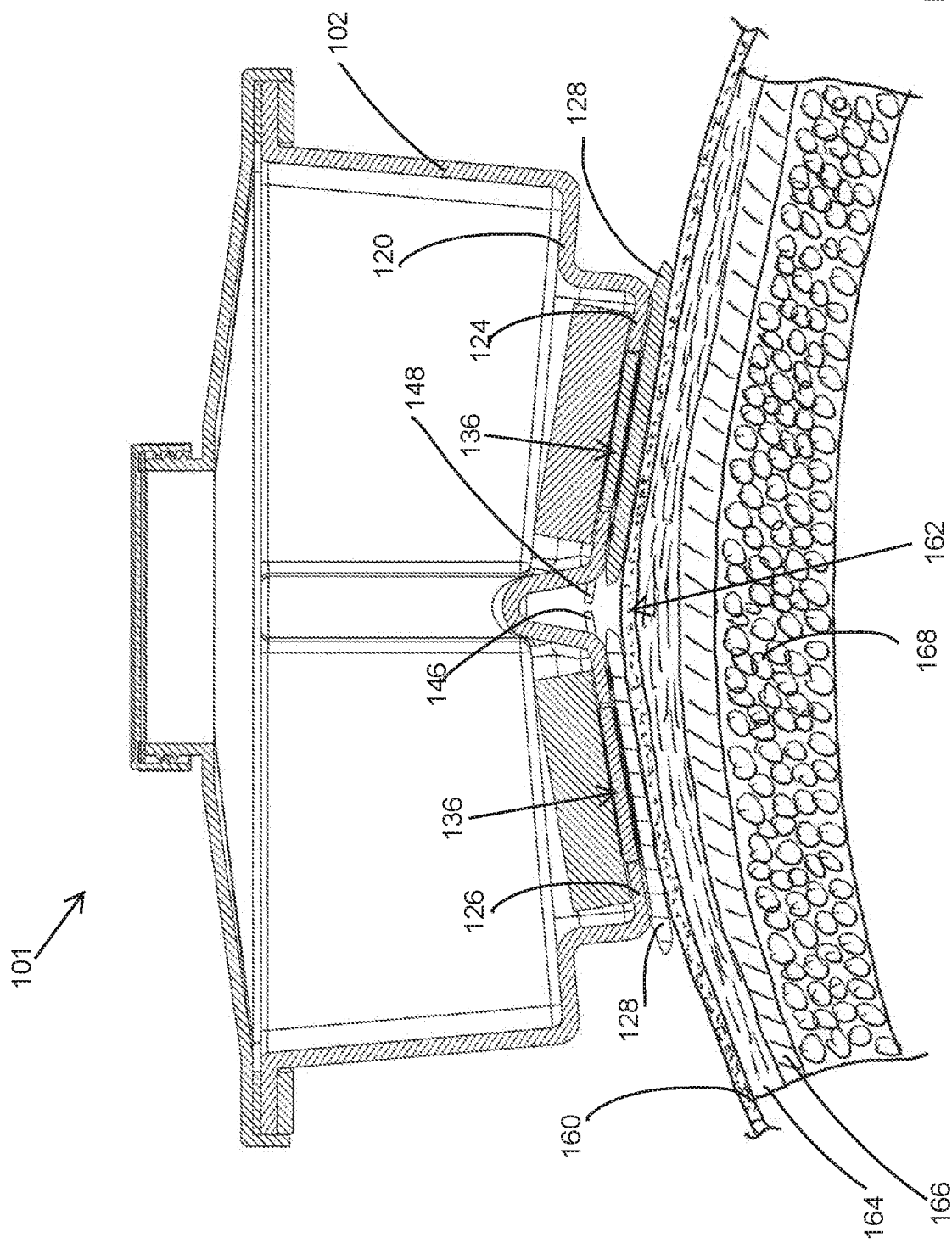
FIG. 6 shows a cross-sectional view of the applicator applied over a targeted area of the skin.

FIG. 6 shows a cross-sectional view of the applicator 101 applied over a targeted area of the skin with a liner 160 between the cooling plates 128 and the targeted area 162 of the skin. The current or power to the two TECs 136 may be provided by first and second wires 146 and 148, along with other wires for temperature sensors 150, not shown, which may be combined to form the cable 112. The cable 112 may have a distal end forming the plug 113 adapted to electrically couple to the power supply 114 to power the TECs 136. The liner 160 may be soaked with antifreeze solution to protect the targeted skin from freeze damage such as freezer burns. The two pods 124 and 126 may protrudes from the base 120 of the container 102 and may be configured so that the adjacent cooling plates 128 may have an obtuse angle to better contour the curvature shape of the user's abdomen, flanks, buttocks, back, chin, foot, inner and outer thighs, and the like. The cooling plates 128 may be shaped and size to contour the smaller portions of the body such as lower face, submentum, and neck as well.

The cross-sectional view shows the targeted area of the skin 162 including an epidermis layer 164, a dermis layer 166, and a subcutaneous adipose layer 168. In general, the epidermis layer may be also described as the surface layer of the skin, and the subcutaneous layer 168 may be also described as the fat cells. When a targeted area of the skin is cooled at a predetermined cool temperature range for a period of time, a portion of the subcutaneous layer (fat cells) may freeze or crystalize. In general, the fat cells may freeze at an elevated temperature compared to its top epidermis and dermis layers such that the fat cells underneath the epidermis and dermis layers may crystalize or freeze without damaging the epidermis and dermis layers.

Figure 7:
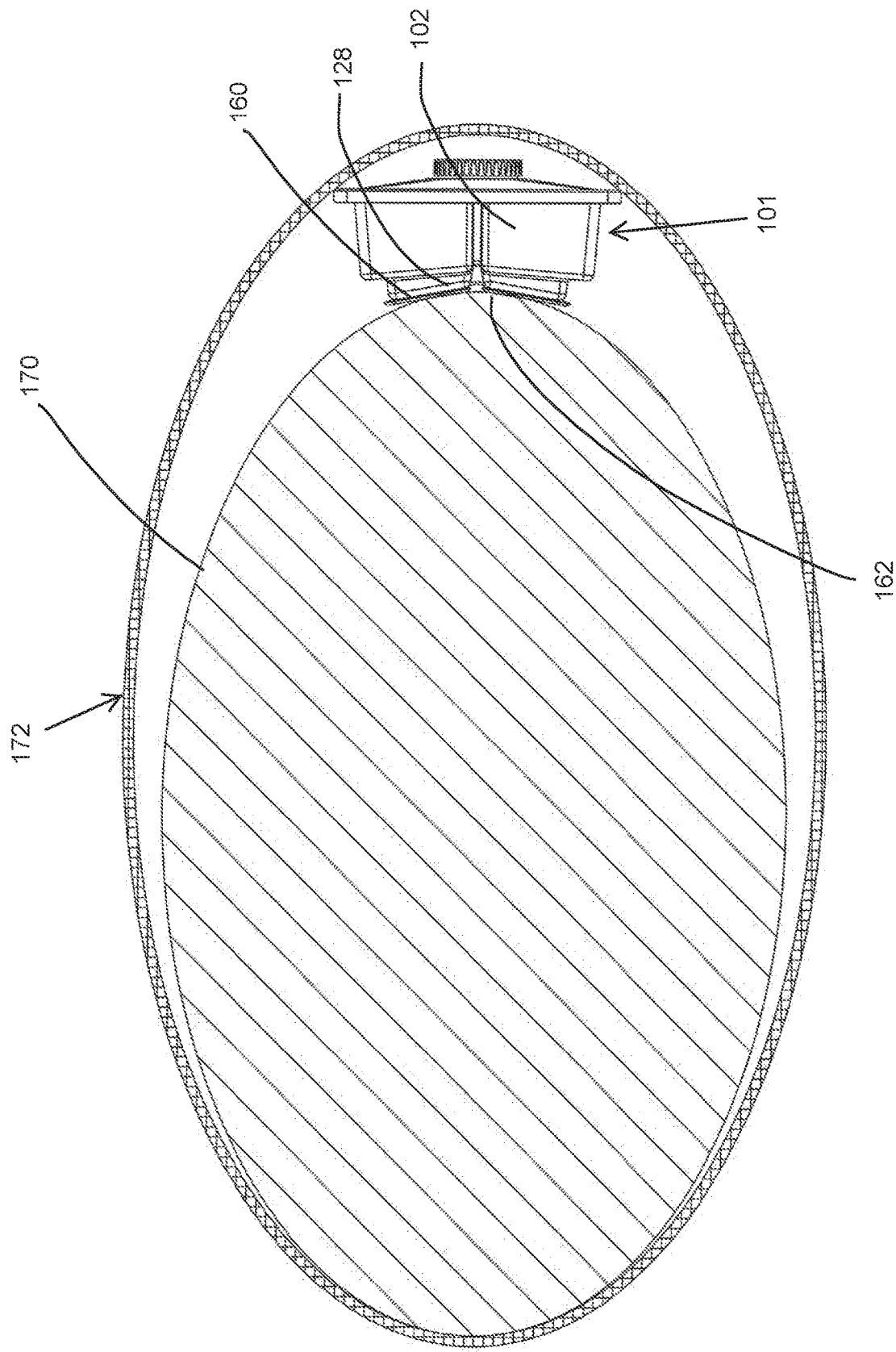
FIG. 7 shows a cross-sectional view of a torso with the applicator applied over the targeted area of the skin.

FIG. 7 shows a cross-sectional view of a torso 170 with the applicator 101 applied over the targeted area 162 of the skin with the liner 160 between the applicator 101 and the skin. A strap 172 may wrap around the torso or waist 170 to apply pressure on the applicator 101 to ensure surface area contact between the cooling plates 128 and the targeted area of the skin. The strap 172 may be elastic to provide some tension to apply constant pressure on the applicator 101. The pressure on the skin by the applicator may improve the efficiency of cooling the three layers 164, 166, and 168. The strap may be adjustable and elastic to fit different body types. The container 102 may be made of flexible material such that the container 102 may bulge out when pressed on by the strap 172 to allow the cooling plates 128 to better conform to the outer body contour shape of the torso 170 of the user. This may allow the applicator to conduct heat away from the three layers 164, 166, and 168 more efficiently to shorten the amount of time it takes to cool the fat cells. Alternatively, a number of other clamping mechanisms, belts, and an inflatable cuff known to one skilled in the art may be used to strap the applicator onto the targeted area of the skin.

Figure 8:
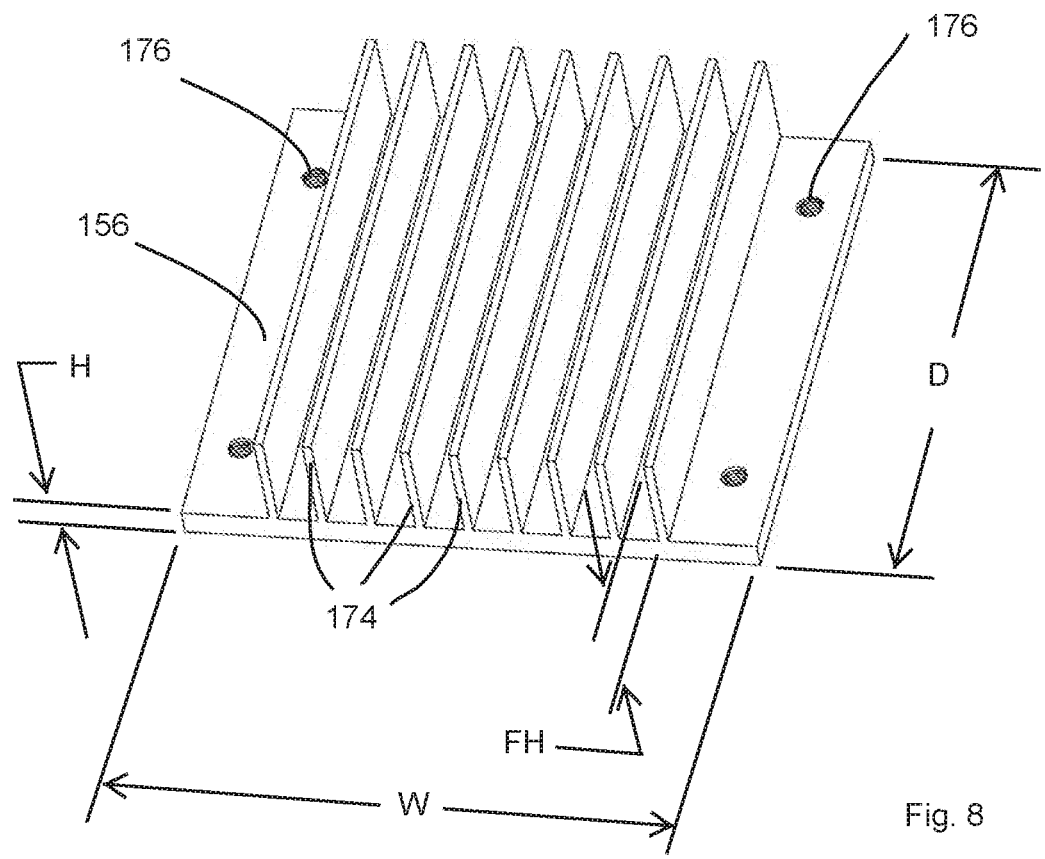
FIG. 8 shows a perspective view of a radiator.
Figure 9:
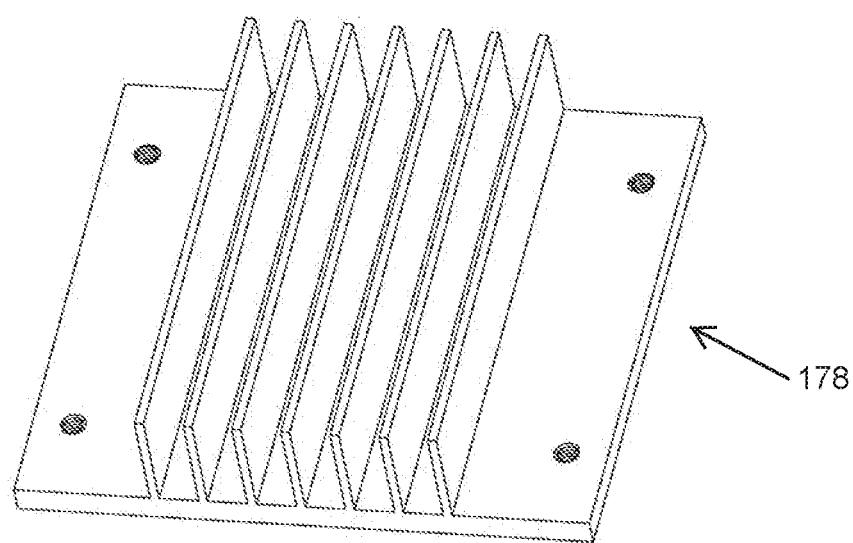
FIG. 9 shows a perspective view of another radiator.

FIG. 8 shows a perspective view of the radiator 130 having a width W, a depth D, a height H, and a plurality of fins 174 with a height FH. The base 156 of the radiator 130 may have holes 176 adapted to receive the couplers 161 to couple the radiator to the cooling plates 138. In the testing the cooling system 100 as discussed below, radiators made of aluminum extrusion with the following dimensions were used: W≈2.5" (63.5 mm), D≈2.5" (63.5 mm), H≈(3.5 mm), and with nine (9) fins having FH≈0.43" (11.0 mm). It is within the scope of this invention to use a radiator with alternative W, D, H, and FH dimensions to dissipate the desired amount of heat from the hot side of the TEC. Moreover, the number of fins 174 used in the radiator may be adjusted to dissipate less or more heat from the TEC depending on the application. For instance, FIG. 9 shows a radiator 178 with seven (7) fins instead of the nine (9) fins utilized in the radiator 130. With less fins, less heat may be dissipated away from the hot side of the TEC such that the coolant within the container 102 may remain cooler for a longer period of time versus the radiator with nine fins. On the other hand, the cold side of the TEC may not get as cold with the seven fins compared to nine fins. Alternatively, utilizing a more thermally conductive material for the radiator such as cooper may also improve the efficiency of radiating heat away from the hot side of the TEC.

Figure 10:
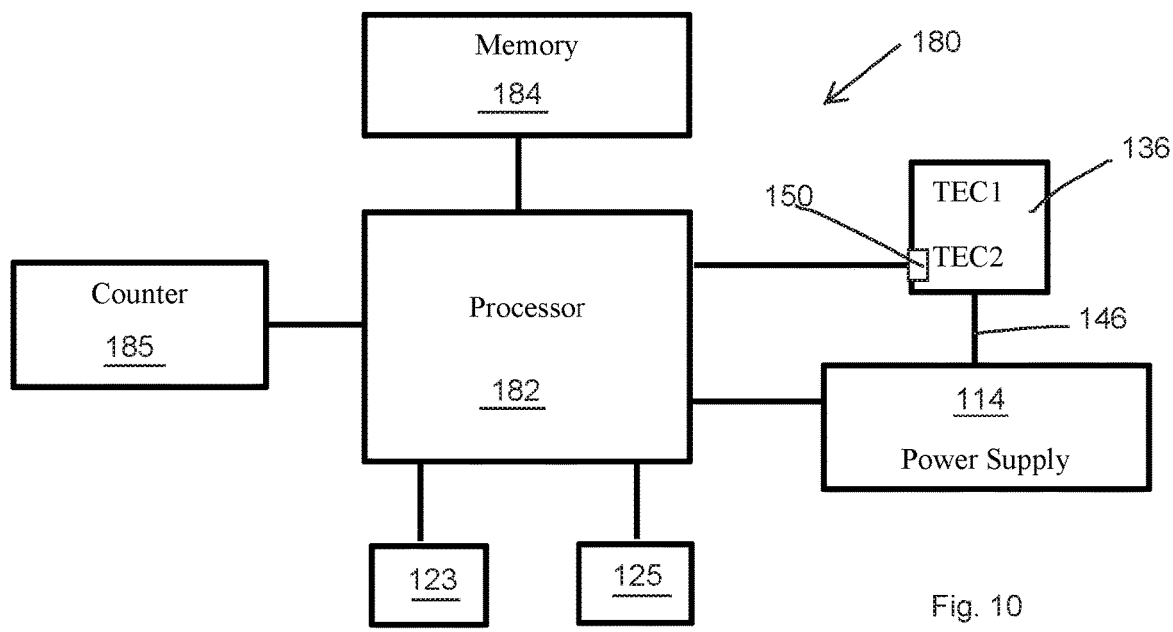
FIG. 10 shows a block diagram of a controller.

FIG. 10 shows a controller block diagram 180 adapted to operate the applicator 101. The controller 180 may include a processor 182 communicably coupled to the power supply 114, a memory 184, one or more TECs 136, and the corresponding temperature sensors 150 to measure the temperature of the corresponding TECs 136, the temperature sensor 123 to measure the temperature of the coolant, and the sensor 125 to measure the coolant to determine if the coolant is an authenticate coolant or not. The processor 182 may be also communicably coupled to a counter 185 configured to keep track of number of times the applicator 101 has been used. The processor 182 may control the power supply 114 to provide power to the TECs 136 through the wire 146.

Testing Sample Applicator:

For testing purposes, an applicator similar to the drawing shown in FIGS. 1 and 2, was constructed with a flexible container configured to hold about 104 oz of coolant. Two TEC1-12712 rated at 12V and 12 amp each were used with a square dimension of 40 mm (width)×40 mm (height)×3.2 mm (depth). The hot side of each of the TEC1 was thermally coupled to the radiator 130, generally described in FIG. 8, having W of about 2.5" (63.5 mm), D of about 2.5" (63.5 mm) with nine (9) fins having a height of about 11.0 mm. The cold side of each of the TEC was thermally coupled to the cooling plate having a rectangular dimensions of about 3.9" (100 mm)×about 3.15" (80 mm). Both the radiators 130 and the cooling plates 138 are made of aluminum material.

Thermal paste were used to ensure good thermal conductivity amongst the radiator 130, TEC1s, and the cooling plate 138. The width of the cooling plates and the radiators are both wider than the square opening to substantially seal around the square opening. Screws were used to couple the radiators and the cooling plates together to ensure that the radiator and the cooling plate remained in good thermal contact. The two wires 146 and 148 from the two TECs and the wires for the temperature sensors were routed to form the cables 112. Sealant was applied over the screws, and between the radiator 130 and the base 120 of the container, and between the cooling plates 138 and the underside of the base 120 to substantially prevent the coolant from leaking from the container.

Figure 11:
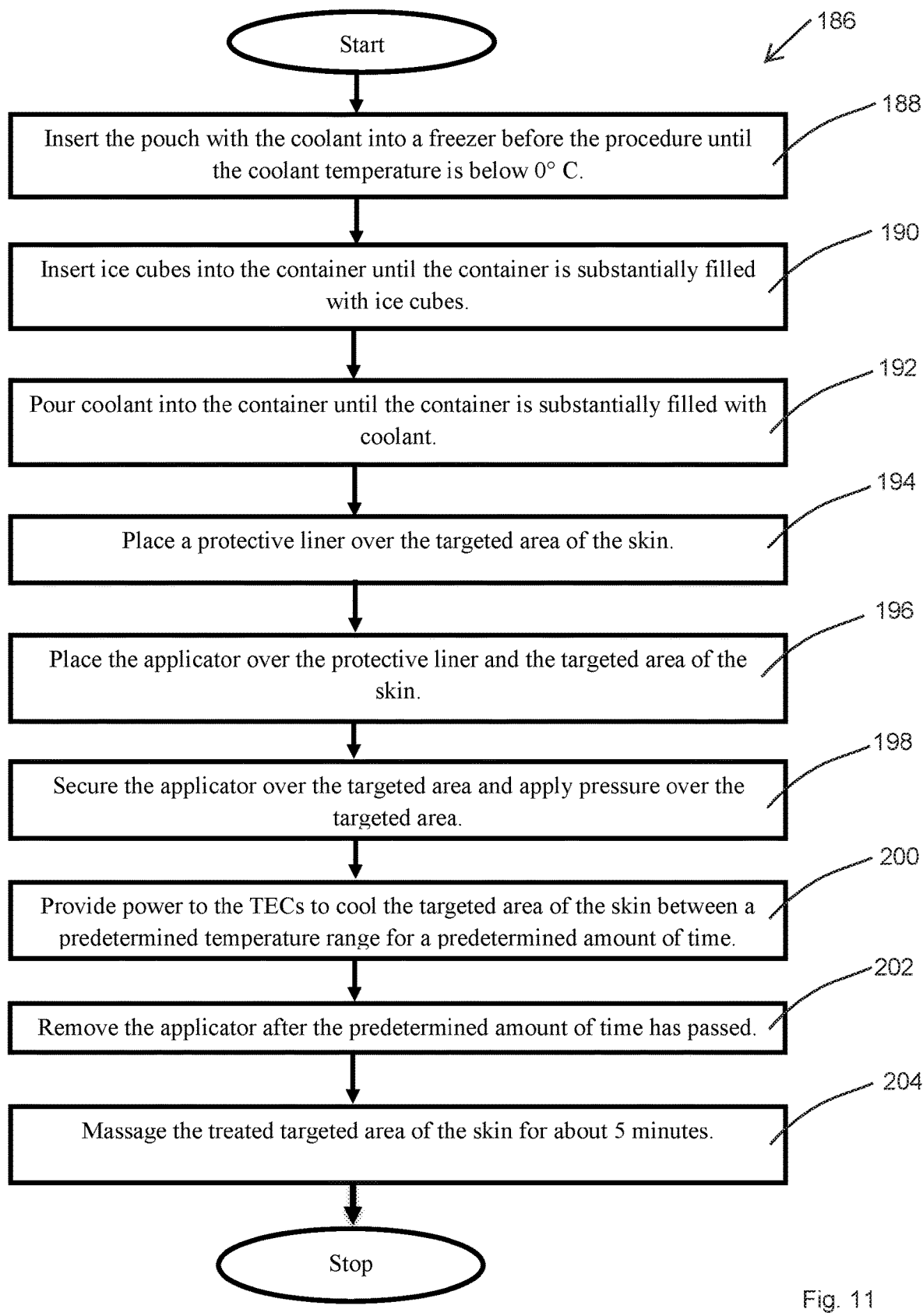
FIG. 11 shows an exemplary flow chart relating to the cooling procedure.

FIG. 11 shows a flow chart 186 related to the cooling procedure. In step 188, in reference to FIG. 2, in preparation for the cooling procedure, the pouch 117 filled with coolant may be inserted into a freezer for several hours before the procedure to allow the coolant inside the pouch to cool below 0° C. (32° F.). The coolant may include antifreeze additive which lowers the freezing point of water-based liquid. A variety of antifreeze additive may be added to liquid such as water to lower the freezing point. For example, antifreeze additive may include one or more of the following solutions, such as, ethyl alcohol, isopropyl alcohol, methanol ethylene glycol, propylene glycol, and glycerol. For instance, from about 5% to about 50% by volume of 70% proof isopropyl alcohol may be mixed with water to form the second portion of the fluid coolant that is fluid below 0° C. so that the coolant may be poured into the container such that the coolant fills the gap between the ice cubes. A number of different mixture combination of antifreeze and water may be formed to formulate the fluid coolant so that the coolant remains fluid below −15° C. or below −20° C. so that the mixture of the first portion of the solid coolant such as ice cubes and the second portion of the fluid coolant inside the container is below 0° C., or below −10° C., or below −15° C. such that the mixture substantially remains cool below about 15° C. after the procedure is done.

In step 190, the first portion of the solid coolant was inserted into the applicator. In the test, about 1,376 grams of ice cubes were inserted into the container 102. Note that with the cover opened, the applicator 101 can hold about 104 oz of water. In step 192, the second portion of the fluid coolant was poured into the applicator. In this test, the applicator 102 was filled with about 1,414 grams of fluid coolant. The fluid coolant used in this test was formulated by using a blender to crush about 1018 grams of ice cubes with about 400 grams of chilled rubbing alcohol in a bottle. In preparation for this test, a bottle of rubbing alcohol containing about 70% proof isopropyl alcohol was placed inside a freezer for more than 24 hours before the test was conducted. The chilled rubbing alcohol was still liquid and the measured temperature was about −11° C. The combination of ice cubes and chilled rubbing alcohol in the amount noted above were crushed using a household blender until the mixture was slushy yet fluid so that the coolant could be readily poured into the applicator. After the blending was over, the coolant measured about −17° C. Even at this low temperature (−17° C.), the coolant was still fluid so it poured into the container through the opening with minimal clogging. The measured temperature of the ice cubes and the fluid coolant inside the applicator was about −15° C. After the container was filled with ice cubes and fluid coolant, the cover 108 was placed over the opening 116. As such, a total of about 2,790 grams of ice cubes and fluid coolant, which is total of about 98.4 oz were poured into the applicator having a capacity of about 104 oz. On a side note, blending ice with chill water at about 0° C. without the antifreeze using a blender may make the coolant slushy but the coolant may clung together such that it may be bit troublesome to pour the slushy coolant into the opening of the lid. Note that blending ice cubes with chilled water, however, is within the scope of this invention.

In step 194, a protective liner was placed over the targeted area, which was the upper abdomen. The protective liner was 42 cm×34 cm rectangular shape, which was soaked with antifreeze additive to protect the skin from freezer burn. In step 196, the applicator was placed over the targeted area. A thermocouple was placed between the cooling plate and the protective liner to measure the temperature of the cooling plate.

In step 198, the applicator was secured over the targeted area of the skin using an elastic strap wrapped around the upper abdomen around the torso. The strap substantially ensured that the applicator did not move around relative to the targeted area of the skin. The initial surface temperature of the skin was about 32° C. With the coolant temperature inside the container being less than −15° C., the temperature of the cooling plates dropped even without any power to the TECs.

In step 200, power was provided to the TECs to cool the targeted area of the skin. Power can be provided by connecting the electrically cables to a PWM power supply to supply DC current to the two TECs. The power supply was then turned ON and OFF several times to further lower the temperature of the cooling plates within a temperature range of between 0° C. and −4° C. In other words, the power supply was turned ON when the temperature rose to 0° C. and it was turn OFF again when the temperature dropped to −4° C., and vice versa. At about 60 minutes into the procedure, most of the ice in the container had melted, which may indicate that the temperature of the coolant has warmed up from the initial temperature of about −15° C. to about 0° C. The test continued in this manner for another 15 minutes for a total of about 75 minutes. During the last 15 minutes, as the temperature of the coolant in the container rose, the power supply was mostly ON, and the applicator was able to maintain the temperature of the cooling plates from about 0° C. to about −2° C.

In general, it has been observed that colder the coolant temperature, the TEC may cool the cooling plates to a lower temperature. Moreover, colder coolant temperature allows for a longer period of cooling treatment procedure. As such, the power to the power supply may be turned ON and OFF more frequently initially when the coolant temperature is cooler, such as below −10° C., as the radiator can quickly dissipate the heat from the TEC at a lower temperature. Conversely, as the coolant temperature rises, the power to the TEC may be turned ON and OFF less frequently to maintain the desired cooling plate temperature. And once most, if not all, of the ice cubes in the container melted, the power to the TEC may be turned ON continuously. As such, the fluid coolant may be provided in a variety of different mixtures depending on the cooling treatment application. For instance, for shorter cooling treatments, the fluid coolant may be chilled water near the freezing point; and the fluid coolant may also be a blend of crushed ice with chilled water. For longer cooling treatment cycle or if colder cooling plate temperature is required, the fluid coolant may be a blend of crushed ice with anti-freezing liquid or any combination thereof. Alternatively, the predetermined amount of coolant may be entirely of fluid coolant formed from a blend of crushed ice cubes and antifreeze ingredient. As such, the percentage by mass between the solid coolant and fluid coolant may vary depending on the application. For instance, 0% by mass of solid coolant and 100% by mass of fluid coolant is within the scope of the invention, as well as 100% by mass of solid coolant and 0% by mass of fluid coolant, and any combination of ratio between these two extreme ratios.

Note that a variety of factors may affect the performance of the applicator such as the efficiency of the thermal materials used for the radiators and the cooling plates, using copper material versus aluminum, along with the construction of the radiators such as a number of fins, and the efficiency of the thermal contacts among the radiator, TEC, and the cooling plate. A variety of other factors can affect the temperature differential between the coolant and the cooling plates, such as the room temperature, the area of the body the applicator is being used, the body fat content, and etc. As such, the temperature ranges discussed above in regards to the applicator for the testing purpose should not be taken as limiting the scope of this invention in anyway. Rather, the temperature ranges discussed relating to this test should be regarded as a general performance of this particular applicator constructed for this test. As such, the test described here should be considered as an exemplary temperature ranges that may be possible when the cooling procedure is conducted in a manner described above and the testing results may vary.

In step 202, once the cooling procedure is done, the applicator was removed from the targeted area of the skin. Shortly thereafter the applicator was removed, the temperature of the coolant was measured, and it was about 15° C. In addition, the targeted area of the skin was examined, and it was noticed that some portion of the targeted area of the skin was red and somewhat hardened indicating that some portion of the subcutaneous fat layer may have harden or frozen.

In step 204, the targeted area of the skin was massaged to soften the hardened area of skin. It may take up to about 5 minutes of massaging for the hardened area of the skin to soften. The massaging of the harden area of the skin may separate the crystalized fat cells from non-crystalized fat cells to allow the natural immune system to remove the crystalized fat cells more effectively, and this may allow the targeted area of the skin to reduce the fat cells more evenly. The targeted area of the skin remained red for about 5 hours and it returned to its natural color after about 8 hours.

Figure 12:
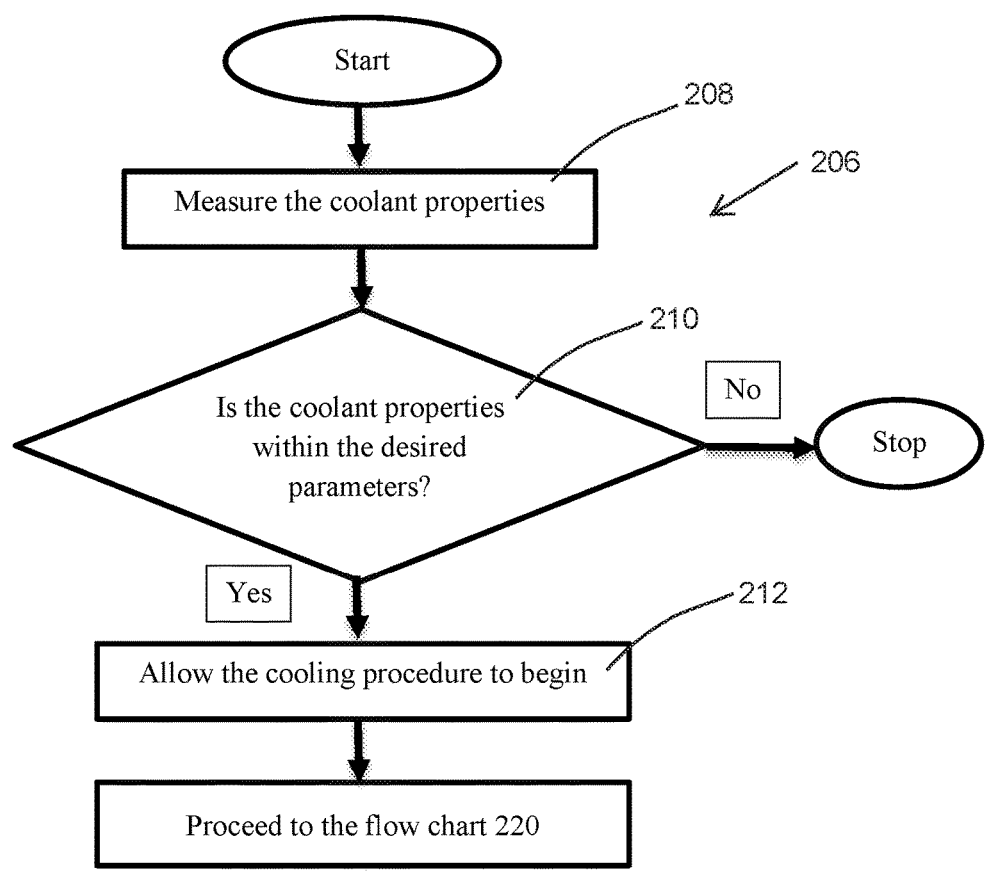
FIG. 12 shows an exemplary flow chart relating an authentication process of the coolant.

FIG. 12 shows a flow chart 206, which may be a subset of the step 194 of the flow chart 180. The flow chart 206 is directed to detecting whether an authorized coolant is used with the applicator 101. In step 208, the sensor 125 may measure the properties of the coolant poured into the container. In step 210, the processor may compare the measured properties of the coolant versus one or more specified properties the coolant should have stored in the memory 204. The specified properties of the coolant may be a variety of one or more factors such as electrical conductivity of the coolant and/or the salt level. For instance, the coolant in the pouch 117 may include a predetermined percentage by mass of sodium compared to the liquid such as water to increase the electrical conductivity of the coolant. The sensor 125 may measure the electrical conductivity of the coolant or any other parameters such as to determine if the coolant is an authorized coolant for not. The processor 202 may compare the measured coolant property with the predetermined property of the coolant stored in the memory. If the measured coolant property does not match the predetermined property of the coolant, then the processor may stop the cooling procedure. On the other hand, if the measure coolant property does match the predetermined property of the coolant, then the processor 202 may proceed with the cooling procedure 212. A variety of other detection methods known to one skilled in the art may be used for the authenticating purposes.

Figure 13:
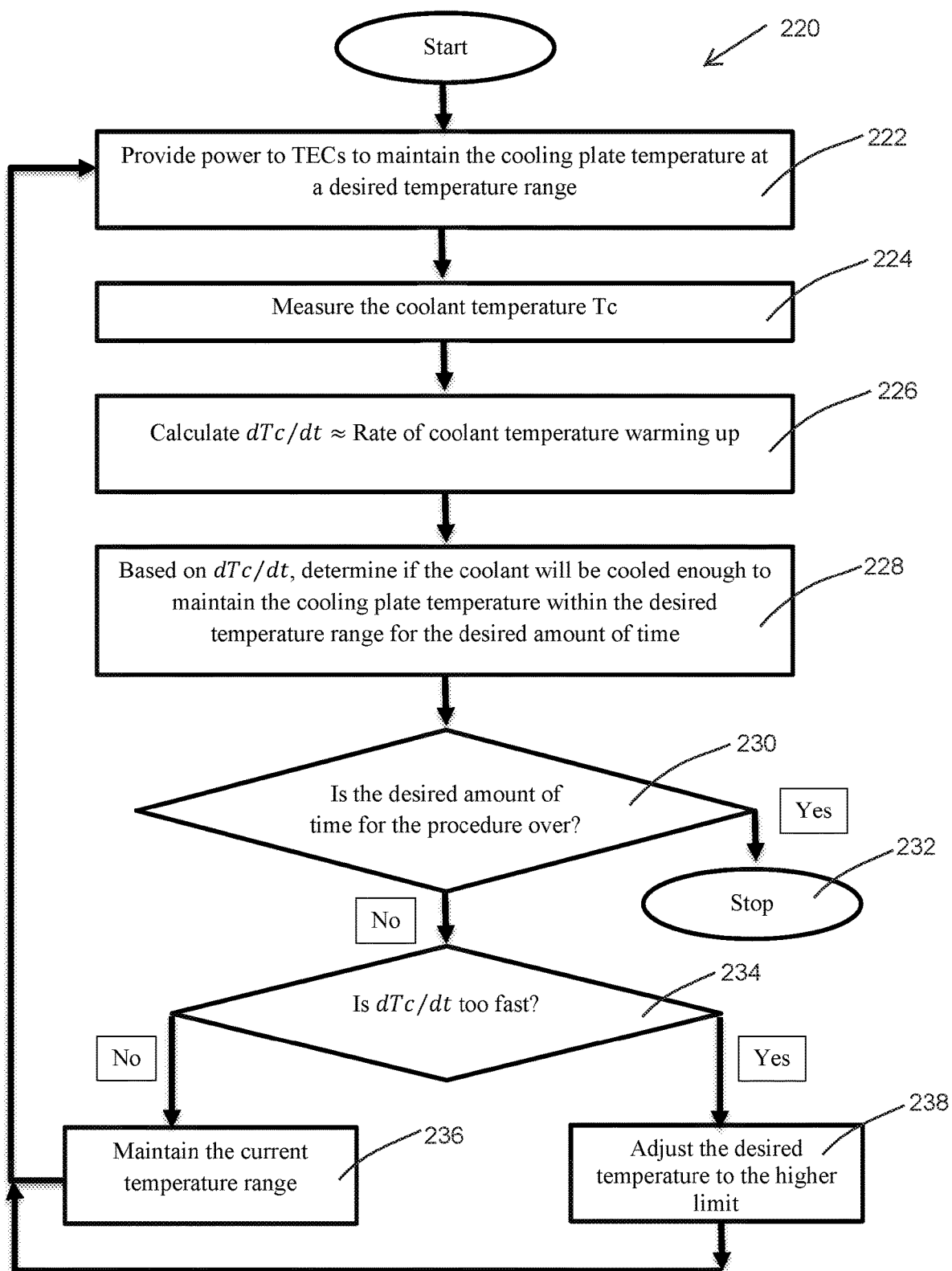
FIG. 13 shows an exemplary flow chart directed to monitoring the temperature of the coolant.

FIG. 13 shows a flow chart 220 directed to monitoring the temperature of the coolant to cool the cooling plates within a predetermined range of cooling temperature for a predetermined period of time. In step 222, the processor 202 may provide power to the TECs 136 to maintain the temperature at the cooling plates within a predetermined rang of lower and upper temperature range. In step 224, the temperature of the coolant may be measured using the temperature sensor 123. In step 226, the processor 202 may then store the measured coolant temperature and the time the measurement was made during the cooling procedure into the memory 204. The processor may then calculate the rate of temperature change in the coolant based on the difference in temperature of the coolant over the time difference, which may be represented as dTc/dt. In step 228, the processor may determine based on dTc/dt, whether the coolant will be cold enough to maintain the cooling plates 128 within the desired range of the lower and upper temperatures for a desired period of time. For instance, depending on the cooling application, the desired time may be between 30 and 120 minutes such as at least 30 minutes, 45 minutes, 60 minutes, 75 minutes, 90 minutes, and 120 minutes. In step 230, if the desired time for the cooling procedure has passed, then the processor 202 may go to the stop command 232. On the other hand, in step 234, if the desired time has not passed, then the processor 202 may determine if the rate of temperature change in the coolant is faster than the desired rate such that the coolant may not be cold enough to maintain the cooling plate at the desired temperature for the desired period of time. In step 236, if the rate of temperature change is too fast, then the processor may adjust the desired temperature to the higher temperature such as maintaining the average temperature to be about −4° C. instead of about −6° C. On the other hand, in step 238, if the rate of temperature change is slower than the desired rate, then the processor may maintain current average temperature of the cooling plates.

Figure 14:
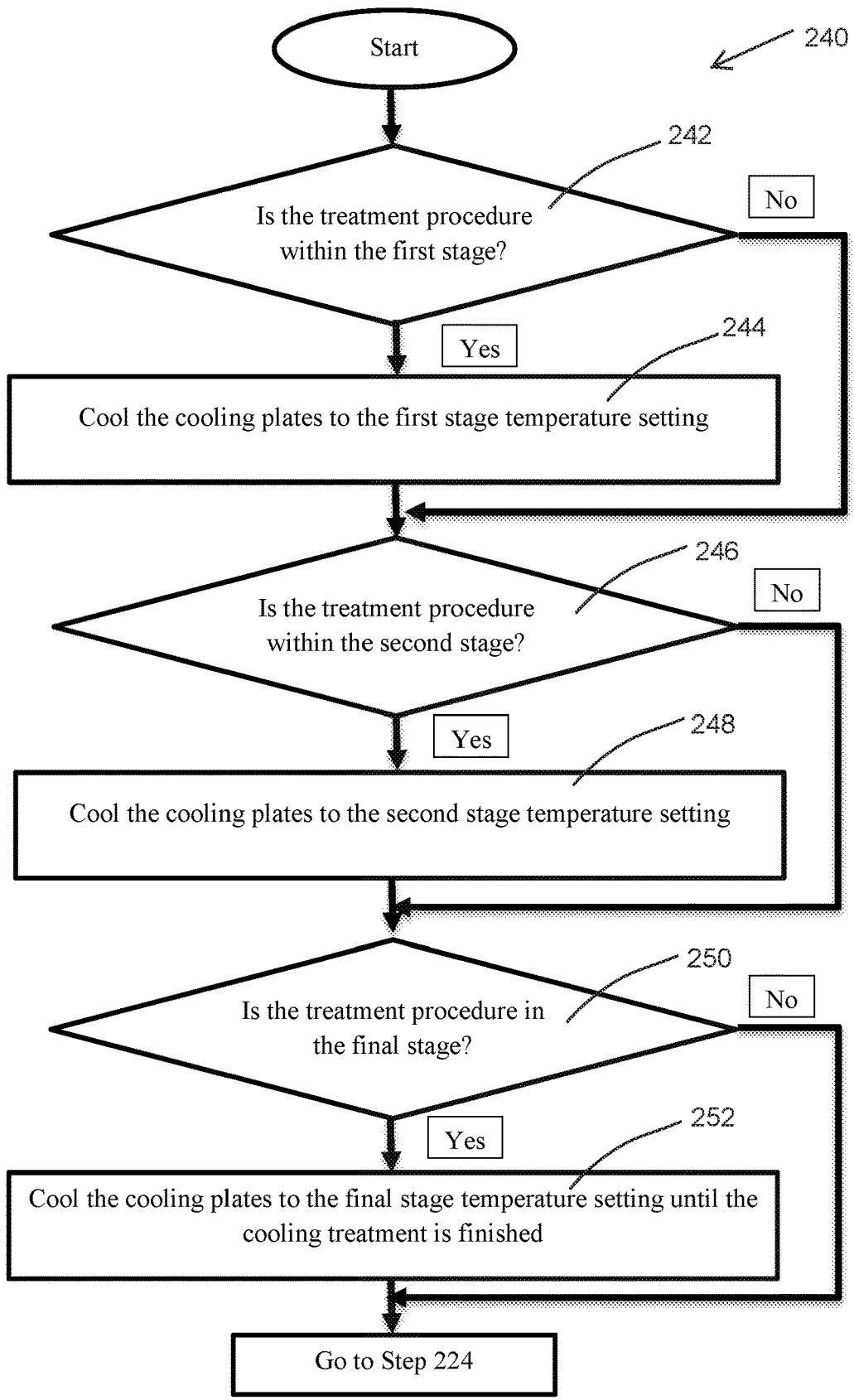
FIG. 14 shows an exemplary flow chart generally directed to transitioning the user into the cooling procedure to mitigate the discomfort due to the cold temperature.

FIG. 14 shows a flow chart 240 with further details of step 222 of flow chart 220 of FIG. 13 generally directed to transitioning the user into the cooling procedure to mitigate the discomfort due to the cold temperature from the cooling plates. In step 242, the processor may determine if the cooling procedure is within an initial stage. In step 244, if the cooling procedure is within the initial stage, then the processor my cool the cooling plates to the initial temperature setting, which may be higher than the normal cooling temperature. This may ease the user into the normal cooling temperature to minimize the discomfort from the cold temperature from the cooling plates. For instance, the initial stage may be from the first 5 minutes to about the first 10 minutes of the procedure; and within this initial stage, the processor may set the initial temperature range from about 0° C. to about −4° C., and in particular from 0° C. to about −2° C., which may be higher than the normal cooling temperature.

In step 246, after the initial stage, the flow chart 240 may include a second stage to further transition the user into the cooling treatment. For instance, the second stage may be between about 5 minutes to about 10 minutes into the procedure; and in step 248, within this second stage, the processor may set the second temperature range that is between the initial stage and the final treatment temperature setting such as from about −2° C. to about −4° C.

In step 250, after the initial and second stages, the processor may determine if the treatment is in the final stage. In step 252, if the treatment is in the final stage, the processor may set the final treatment temperature for the remaining time period until the procedure is finished. For instance, the final treatment temperature range may be set from about −4° C. to about −6° C. After these steps are done, the flow chart 270 may go back to step 224.

Figure 15:
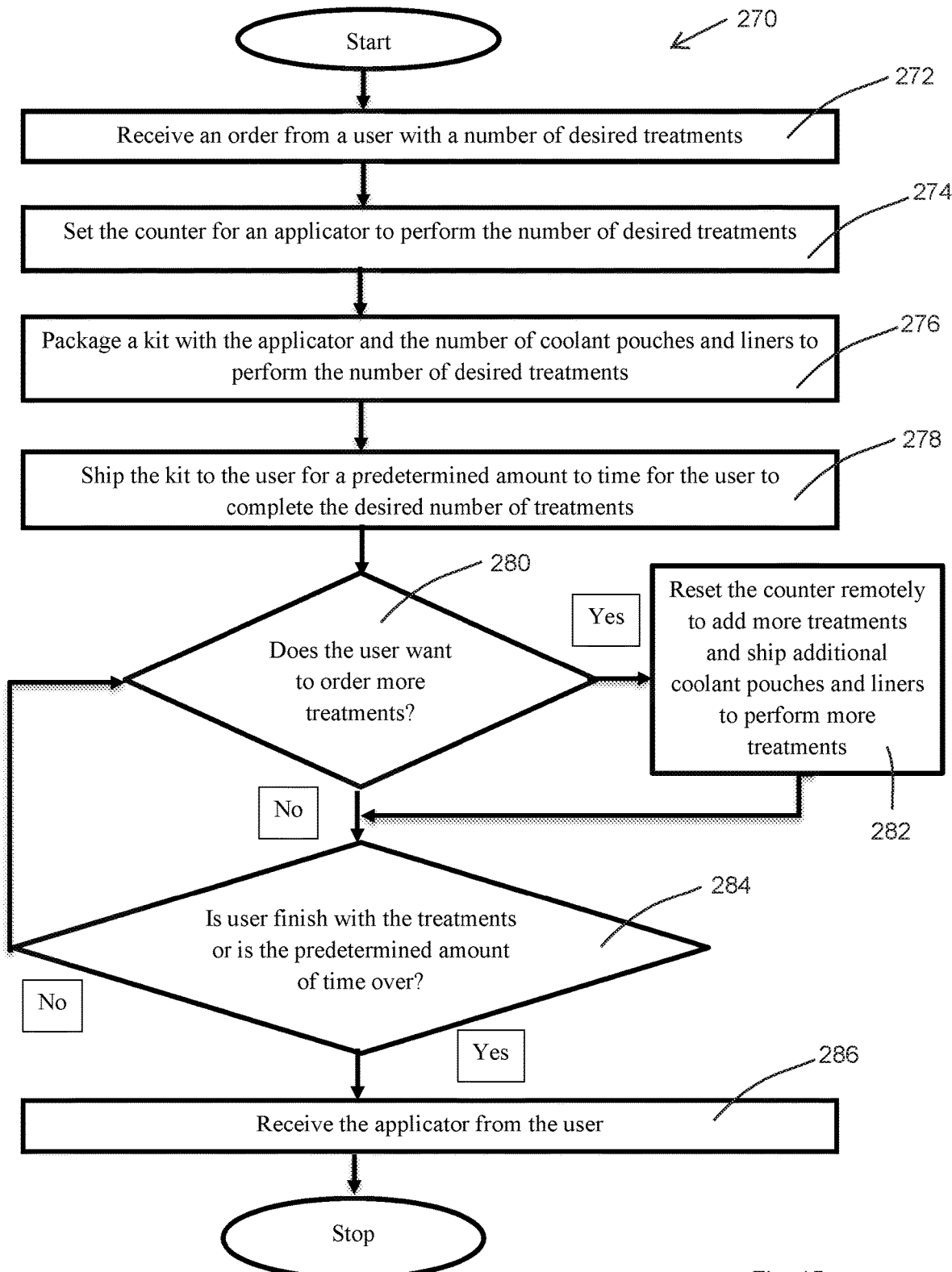
FIG. 15 shows an exemplary flow chart directed to a cooling kit.

FIG. 15 shows a flow chart 270 directed to providing a cooling system 260 to a user. In step 272, an order may be received from a user with a desired number of treatments. In general, the targeted area of the skin may need to be treated more than once to notice a meaningful fat reduction. For example, two or more cooling treatments may be needed in the same targeted area of the skin with the applicator 101 to notice the fat reduction in the targeted area of the skin. Moreover, a variety of different areas of the body may be treated with the applicator 101 such as abdomen, flanks, buttocks, back, inner and outer thighs, and the like. As such, a number treatments the user may order may vary depending on the user.

In step 274, the counter 205 for the applicator 101 may be set to the desired number of treatments as requested by the user in step 272 for a desired amount of time. For instance, if each treatment time is about 90 minutes, the counter 185 may reduce the number of treatment available by one after each 90 minute treatment cycle, and let the user know the number of treatment(s) which is/are left. In addition, the counter 185 may be set to allow the user to rent the cooling system for a sufficient period of time to allow the user to perform all the ordered treatments. In step 276, a cooling system or cooling kit may be assembled including the applicator 101, with a predetermined number of liners and coolants equal to the desired number of treatments ordered by the user. The cooling system may also be comprised of just the liner and the coolant. Each treatment cycle may require the use of one liner and one pouch 117 filled with coolant. As such, if the user orders ten (10) treatments, the cooling system may include an applicator with the counter set at ten (10) treatments, ten (10) liners, and ten (10) coolant pouches.

In step 278, the cooling system may be shipped to the user for a predetermined amount of time to allow the user sufficient time to complete the number of treatments the user ordered. For instance, if the user orders ten (10) treatments in reference to step 272, it may take up to two months to perform the ten treatments at home. As such, the counter 185 may be set to operate ten treatments, and to stop working after a predetermined number of dates such as 60 days from the cooling system is shipped to the user. As such, the applicator may stop working after the desired number of treatments have been performed and/or after the predetermined number of dates have passed. In general, the user may need to wait about 2 to 4 weeks between two subsequent treatments to allow the targeted area of the skin to recover from the prior cooling treatment. For instance, the user may need about one or several months to treat one or more targeted areas several times such that the user may rent the applicator for the desired amount of time. Note that it is within the scope of this invention to remotely reset the counter with regard to the number of treatments and the number of days the applicator may operate in the event that the applicator malfunctions such that the counter needs to reset while the applicator is in user's possession.

In step 280, once the user is finished with the number of treatments the user ordered or the allotted time for the applicator has expired, the user may order more treatment or extend the time allotted for the treatments ordered. If the user orders more treatments or extend the treatment allotted time; in step 282, the processor may remotely add more treatments to the counter 185, and additional coolants and liners may be sent to the user; or the allotted time may be extended.

In step 284, the processor may determine based on the remote access to the counter 185 or whether the allotted time has passed, the processor may determine if the user is finished with the applicator 101, and request from the user whether the user would like to order more treatment. In step 286, if the user is finished with the applicator, then the applicator may be returned to the provider. The provider may then receive the returned applicator and recondition the applicator to the proper working order and rent the applicator as part of the kit for another user.

Figure 16:
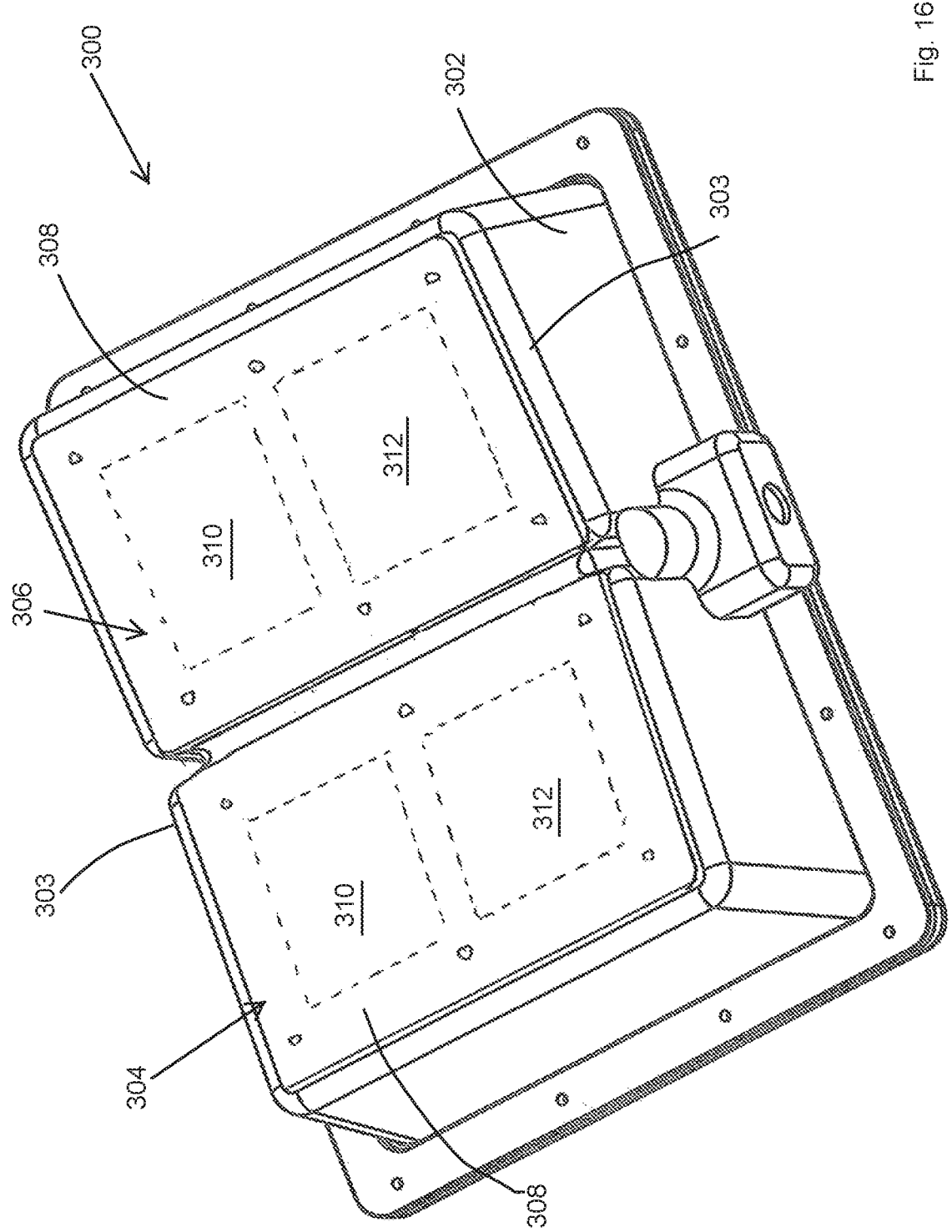
FIG. 16 shows a bottom view of an applicator having a base divided into two cooling pods.

FIG. 16 shows a bottom view of an applicator 300 having a container 302 with a base 303 divided into two pods 304 and 306. Each cooling pod may have a cooling plate 308 thermally coupled to two TECs 310 and 312 underneath the cooling plate 308 represented as dotted lines. Each of the TECs 310 and 312 may be rated at about half of the cooling power as the TEC 136 used in reference to the container in FIG. 5. For instance, the TEC 136 may be rated 12 A at 12V while each of the TECs 310 and 312 may be rated at 6 A at 12V such that the two TECs 310 and 312 may consume about the same amount of power as the TEC 136. However, with the two TECs 310 and 312 having more thermal surface area contact with the cooling plate 308, the cooling may be more evenly distributed to the targeted area of the skin to improve the thermal conductivity between the cooling plate and the targeted area of the skin. Note that container may be formed from a flexible material such that each pod may move independently with respect to the other to improve the thermal conductivity between the cooling plate and the targeted area of the skin.

Figure 17:
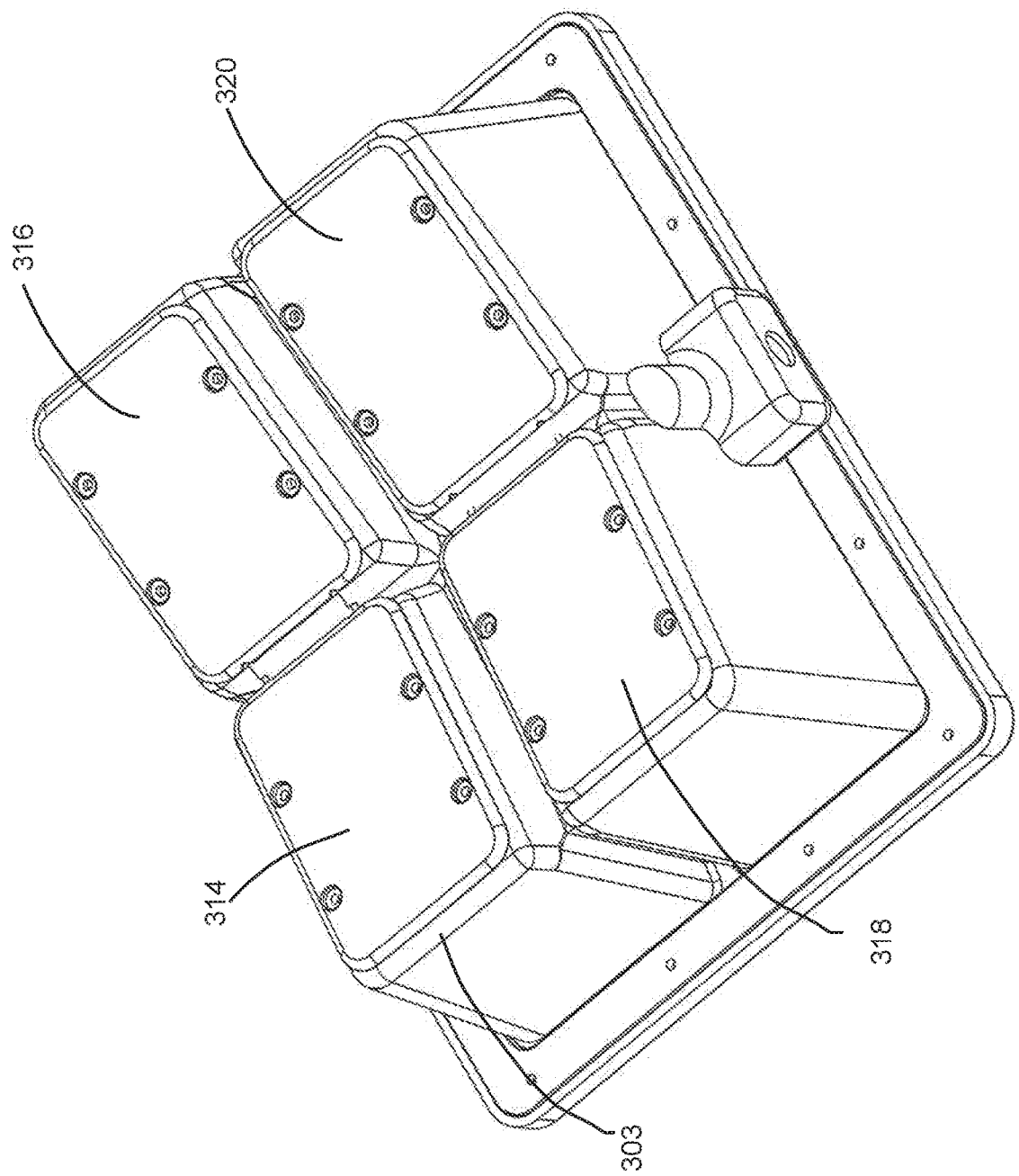
FIG. 17 show that the base of the applicator divided into a plurality of pods.
Figure 18:
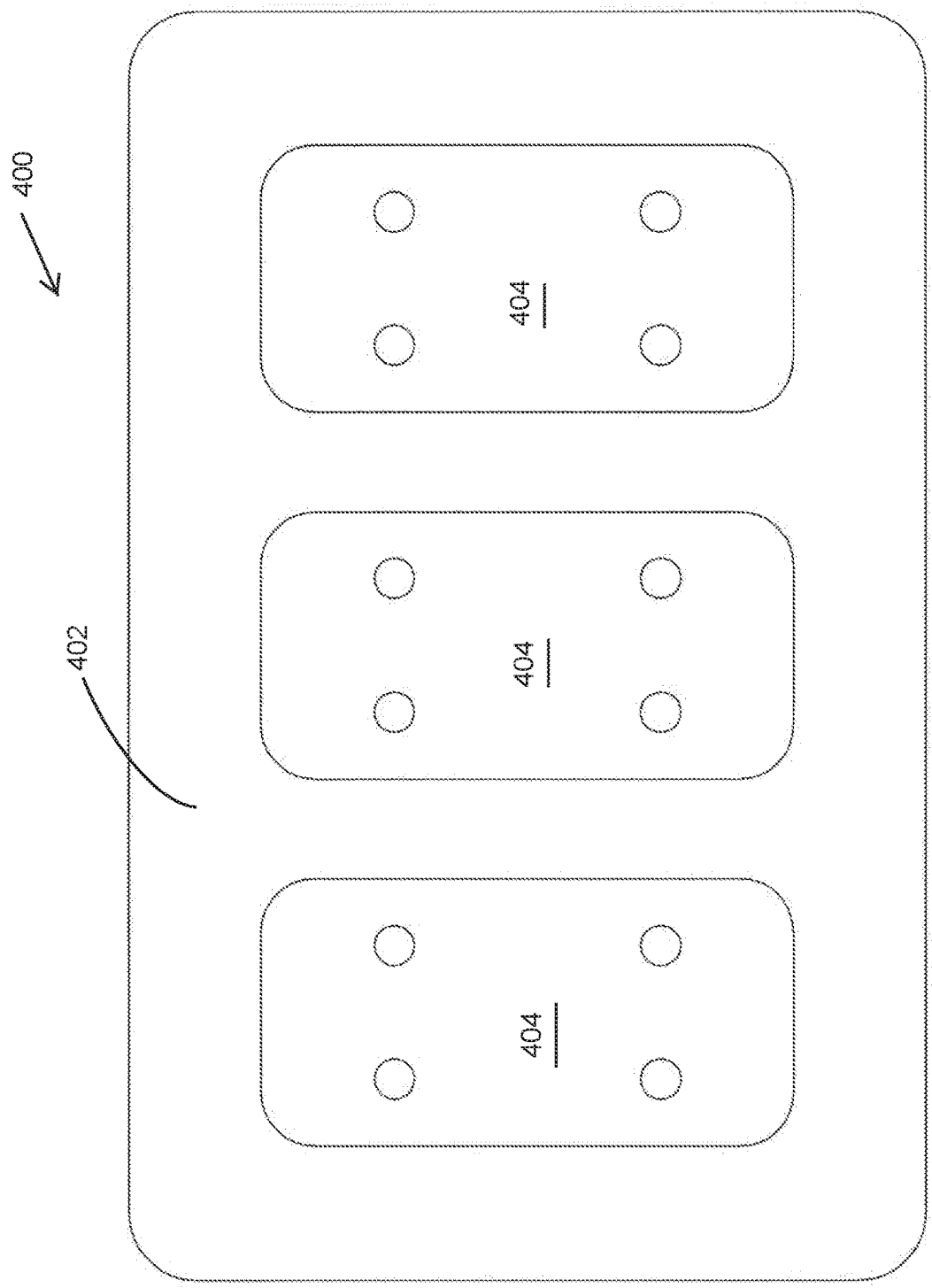
FIG. 18 shows a bottom view of the applicator with another pod configuration.

FIG. 17 show that the base 303 may be divided into four cooling pods 314, 316, 318, and 320 to allow each of the pods to move independently to better contour the surface of the skin. As such, it is within the scope of the invention to have one cooling pods or a plurality of pods in odd or even numbers. For instance, FIG. 18 shows a bottom view of an applicator 400 having a base 402 with more than one cooling pods 402, such as three cooling pods 402, to cover a larger targeted area. The base 402 may be flexible to allow each of the cooling plates 404 to move independently.

Figure 19:
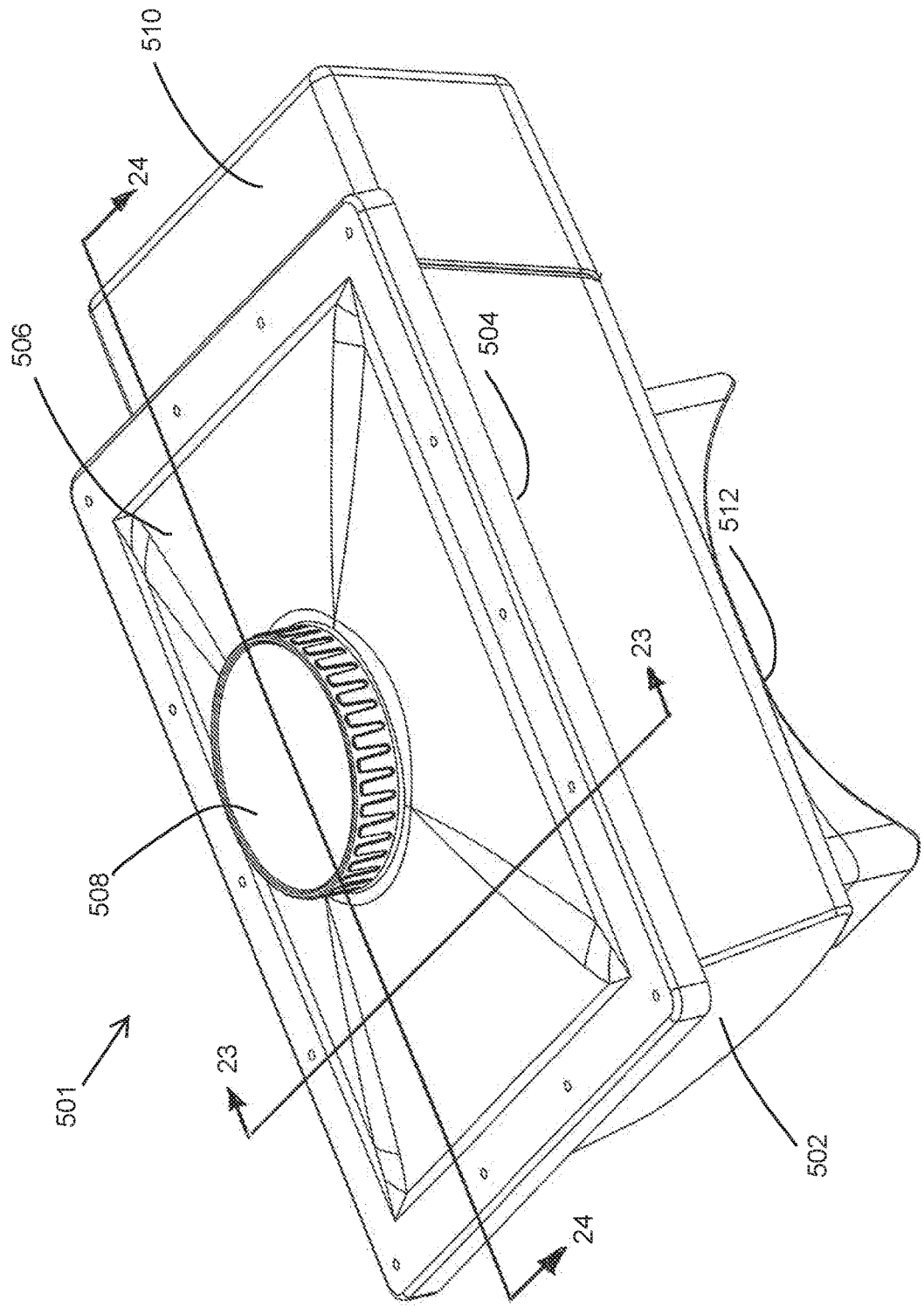
FIG. 19 shows a perspective of another applicator having a chamber configured to draw the targeted area of the skin into the chamber.

FIG. 19 shows a perspective of an applicator 501 including a container 502 having a rim 504 adapted to couple to a lid 506. The lid 506 may have a cover 508 adapted to release from the lid 506. The applicator 501 may have a duct 510 to route the electrical cables having a plug adapted to electrically couple to the power supply similarly shown in FIG. 1. The duct 510 may house a pump (not shown) to generate a vacuum pressure within a chamber 512 as discussed in more detail below. As discussed in reference to FIG. 2, the cover 508 may be removed to insert ice cubes into the container 502 until the ice substantially fills up the container 502, and then the coolant within the pouch 117 may be poured into the applicator 501 to substantially fill in the gap amongst the ice cubes. The container 502 may be formed from a flexible non-porous material such as rubber, or a rigid material, or transparent material, or any other material known to one skilled in the art configured to hold liquid there within. The container may be configured to hold from 60 oz to 140 oz of water; and in particular, from 80 oz to 120 oz of water, and in further particular about 100 oz of water. Accordingly, a cooling system 500 may be comprised of the applicator 501, the power supply 114, the pouch 117 fill with coolant, and the liner 160.

Figure 20:
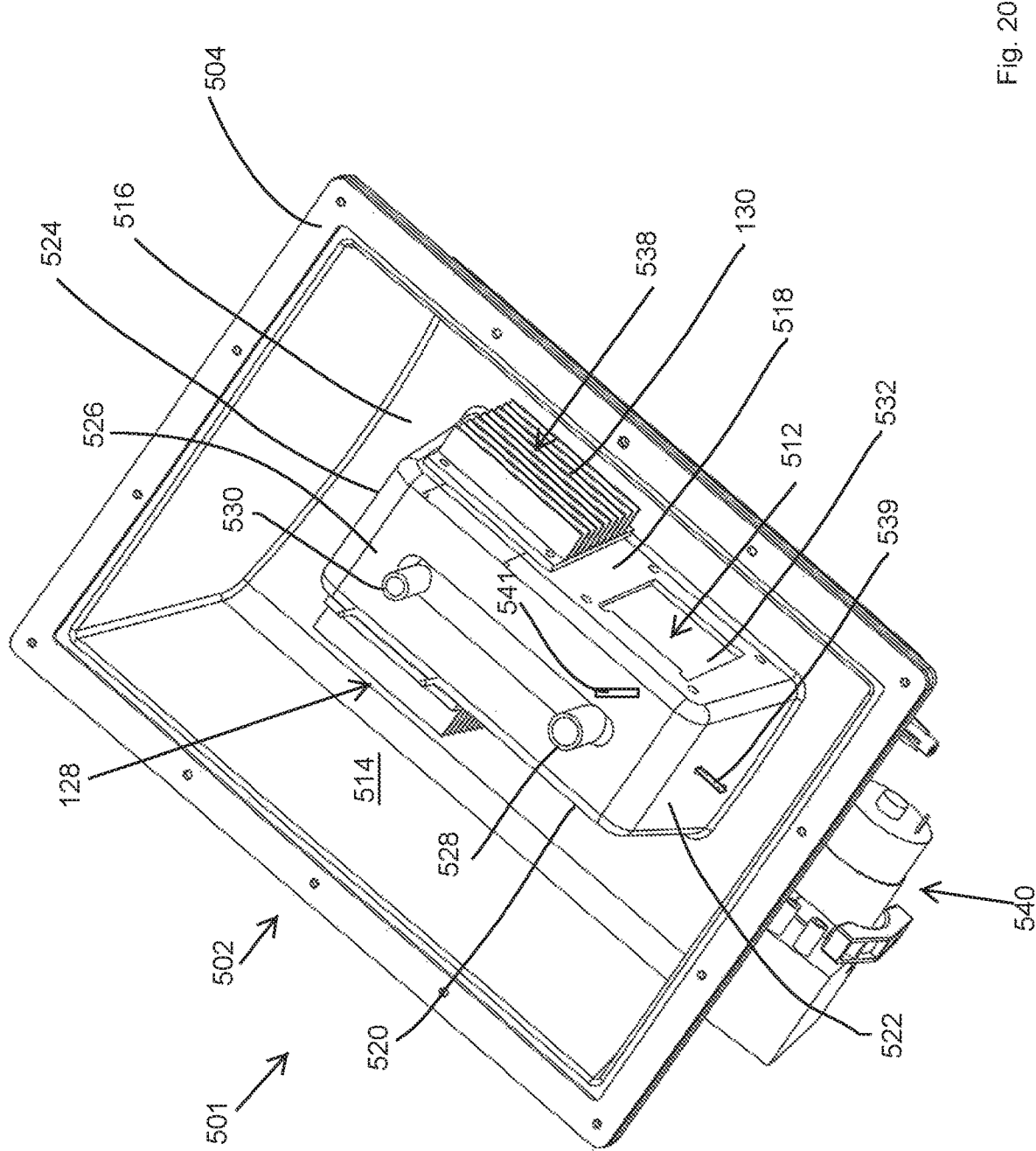
FIG. 20 shows the applicator of FIG. 19 with the lid removed showing the interior space of a container.

FIG. 20 shows the applicator 501 with the lid 506 removed showing the interior space 514 of the container 502. The container 502 may have a base 516 with first and second side walls 518 and 520, respectively, and third and fourth side walls 522 and 524, respectively, conjoining to form a top side 526. The top side 526 may have a first pipe 528 and a second pipe 530. The side walls may form the chamber 512 underneath the base 516. The first and second side walls 518 and 520 may each have one or more openings 532 adapted to receive a TEC such that the cold side faces the chamber and hot side faces the interior space 514 of the container 502 adapted to thermally couple to the radiator 130, as discussed above in reference to FIG. 8. As illustrated in FIG. 20, each of the side walls 518 and 520 may have one or more TEC systems 538. Each TEC system 538 may include a TEC between a cooling plate (not shown) and the radiator 130. In this embodiment, the applicator 501 may have two TEC systems 538 on each of the side walls for a total of four TEC systems 538. Note that in FIG. 20, one of the TEC system 538 has been removed on the side wall 518 and side wall 520 to show the opening 532 adapted to receive the TEC. The container 502 may also include a temperature sensor 539 to measure the temperature of the coolant, and a sensor 541 to measure the coolant to determine if the coolant is an authorized coolant or not.

Figure 21:
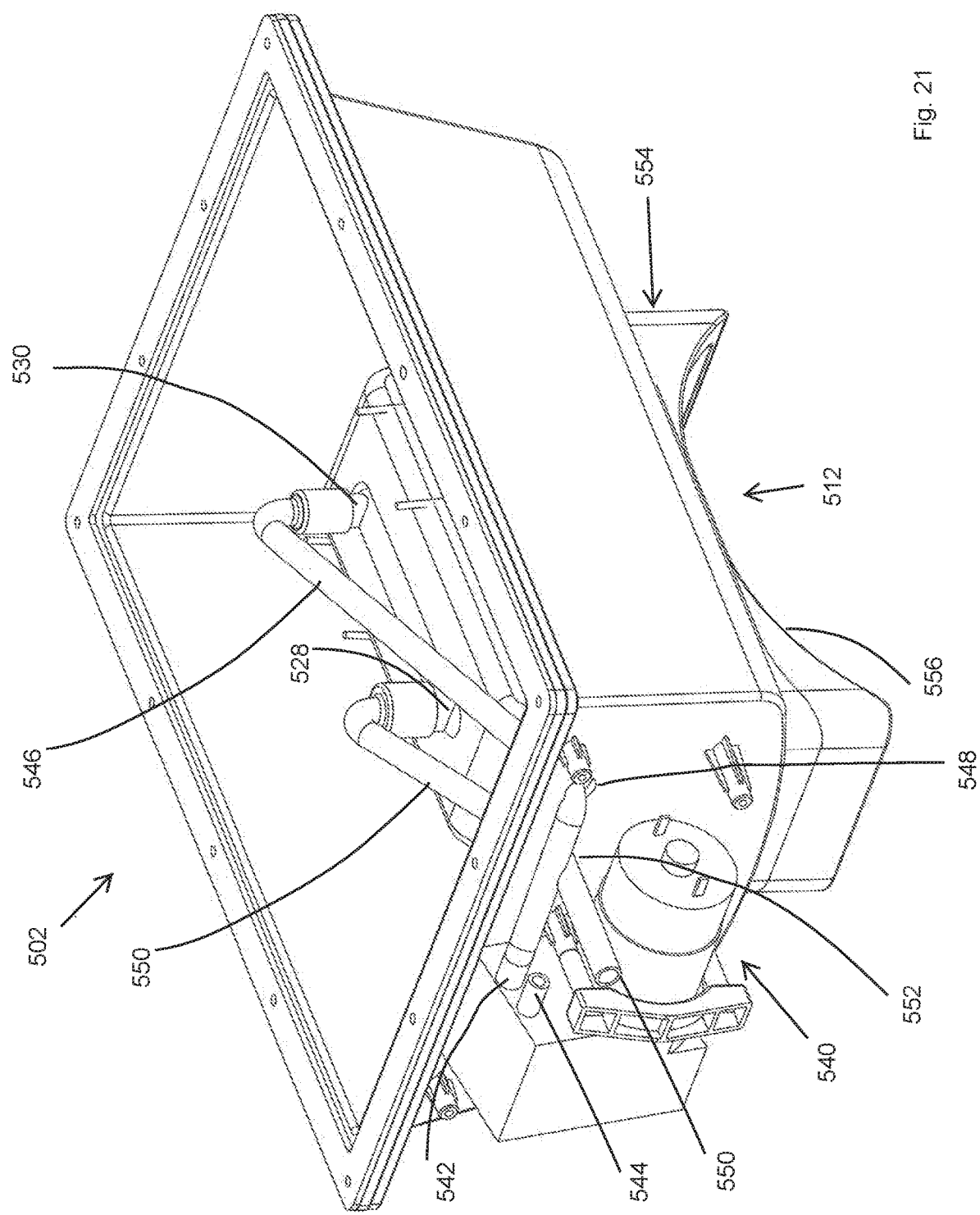
FIG. 21 shows the applicator including a pump to generate vacuum pressure within the chamber.

FIG. 21 shows that the container 502 may include a pump 540 adapted to remove the air within the chamber 512 to generate vacuum pressure within the chamber 512. The pump 540 may have an inlet pipe 542 to receive air and an outlet pipe 544. The applicator may include a first tube 546 coupling the inlet pipe 542 to the second pipe 530 to at least partially remove the air inside the chamber 512. The first tube 546 may be routed through a first hole 548, which may be sealed to prevent the coolant from leaking through the hole 548. The applicator may also include a second tube 550 with one end coupled to the first pipe 528 to rout the electrical wires (not shown) for the four TECs positioned along the first and second side walls 518 and 520, and temperature sensor wires through a second hole 552 and out of the container 502. The electrical and temperature sensor wires may form the electrical cables to provide power to the TECs and to measure the temperature of the cooling plates. The applicator may also include a seal 554 with a lip 556 configured to contour the surface area of the targeted area of the skin. The lip 556 may have a semi-concave configuration to wrap around the round contour shape of the body. Depending on the contour of the body, the seal 554 may be removed and replaced with another seal that better matches the contour of the user's targeted area of the skin.

Figure 22:
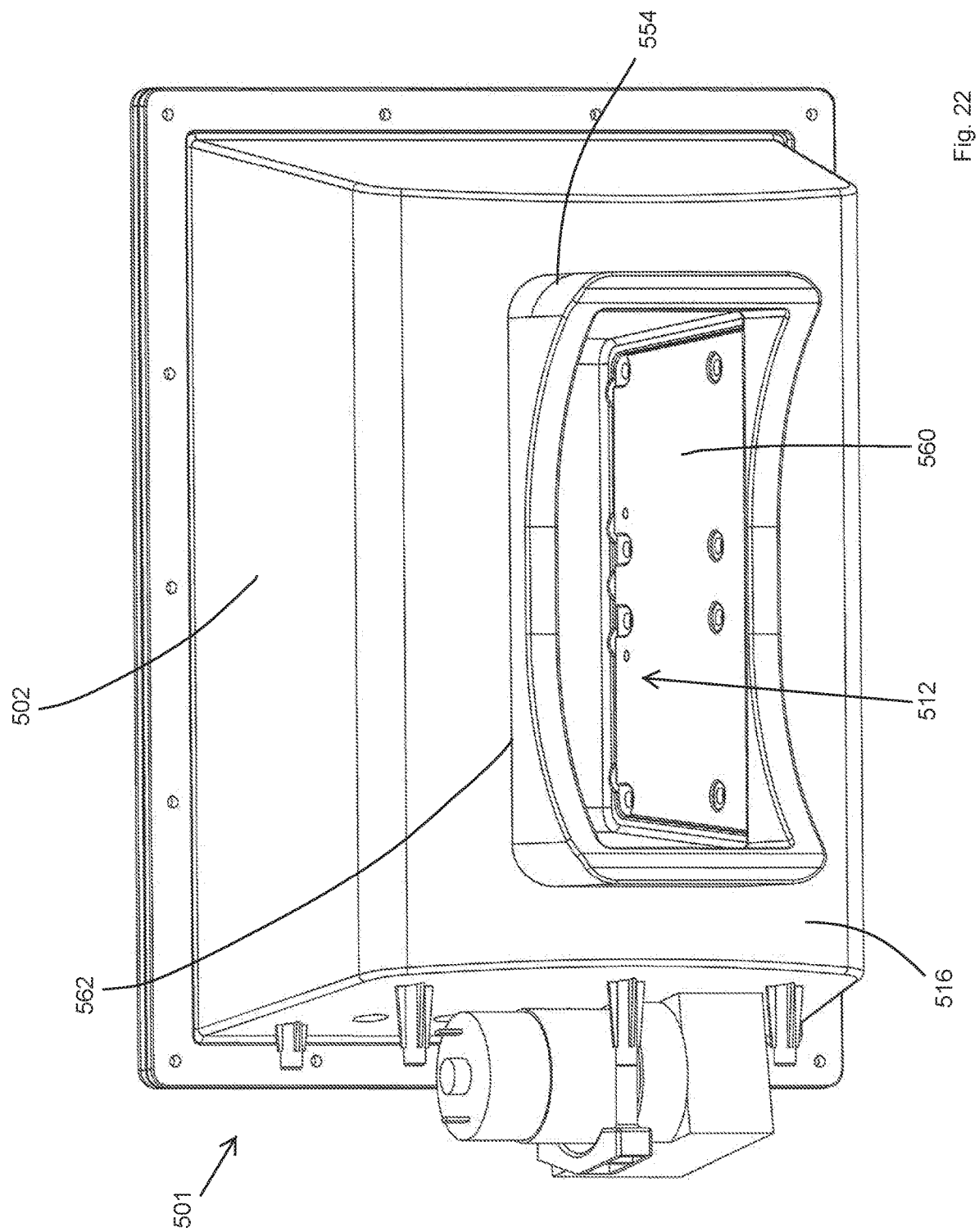
FIG. 22 show a bottom perspective view of the applicator showing the chamber underneath the base of the container.

FIG. 22 show a bottom perspective view of the applicator 501 to show the chamber 512 underneath the base 516 of the container 502. Within the chamber 512, each of the first and second side walls 518 and 520 may have a cooling plate 560 thermally coupled to the two TECs within the openings 532, as discussed in more detail below. The cooling plate 560 may be sealed to the side wall within the chamber to substantially prevent coolant and/or liquid within the container 502 from leaking into the chamber 512 due to the vacuum pressure within the chamber. The seal 554 may have a base 562 that is releasably coupled to the base 516 of the container 502. The seal may be formed from a flexible material such as rubber to form an air tight seal between the seal 552 and the targeted area of the skin.

Figure 23:
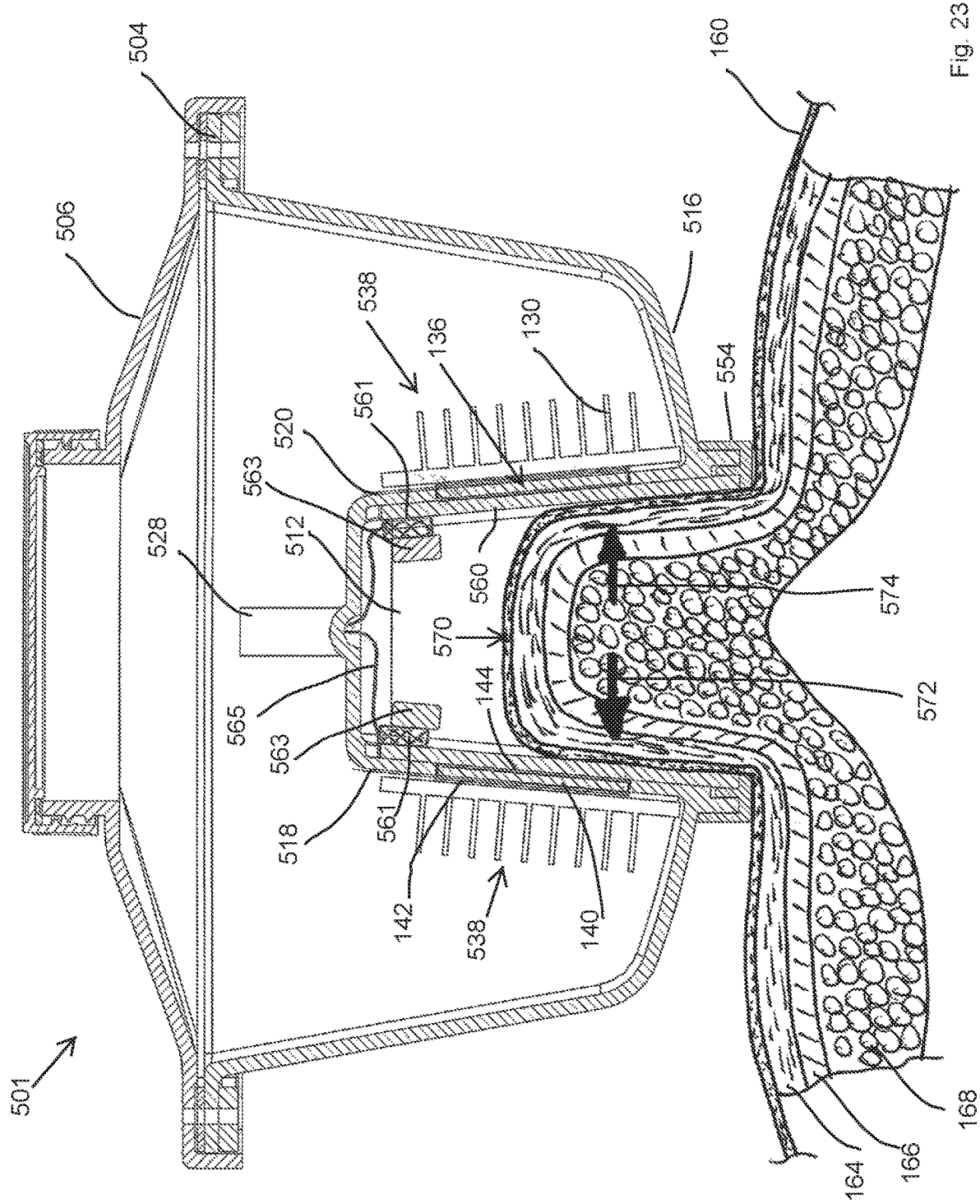
FIG. 23 show a cross-sectional view of the applicator of FIG. 19 along the line 23.

FIG. 23 show a cross-sectional view of the applicator 501 of FIG. 19 along the line 23. The rim 504 of the container 502 may be adapted to couple to the lid 506. The base 516 of the container 502 may have the camber 512 in the form of an inverted "U" shape defined by the first and second side walls 518 and 520 adapted to thermally couple to one or more TEC systems 538. The cooling system may include a TEC 136 between the radiator 130 and the cooling plate 560. TEC 136 may be thermally coupled to the radiator and the cooling plate with thermal paste with the hot side of the TEC juxtaposed to the radiator 130 and the cold side of the TEC juxtaposed to the cooling plate. The radiators and the cooling plates may be sealed to their respective side walls to prevent coolant from leaking into the chamber 512 due to the vacuum pressure. The base 516 of the container 502 may be adapted to releasably couple to the seal 554 to minimize the resistance of the targeted area of the skin being sucked into the chamber 512.

The pump may be draw air out of the chamber 512 through the first pipe 528 to create at least a partial vacuum pressure within the chamber 512 to draw the targeted area of the skin 570 into the chamber 512. This may minimize the gap between the skin and the two adjacent cooling plates 560 to efficiently conduct heat away from the targeted area of the skin through the cooling plates as indicated by the direction arrows 572 and 574. This allows the targeted area of the skin having the three layers 164, 166, and 168 to be folded such that the two outer cooling plates 560 may draw heat away from the three layers 164, 166, and 168 from both sides as indicated by the direction arrows 572 and 574, thereby improving the efficiency of crystallizing the fatty cells 168 located within the folded area of the skin. Each of the cooling plates 560 may be thermally coupled to a temperature sensor 561 held by a bracket 563 to measure the temperature of their respective cooling plates 560. The wires 565 for the TECs 136 and the temperature sensors 561 may be routed within the chamber 512 and through the first pipe 528 to provide power to the TECs and measure the temperatures.

Figure 24:
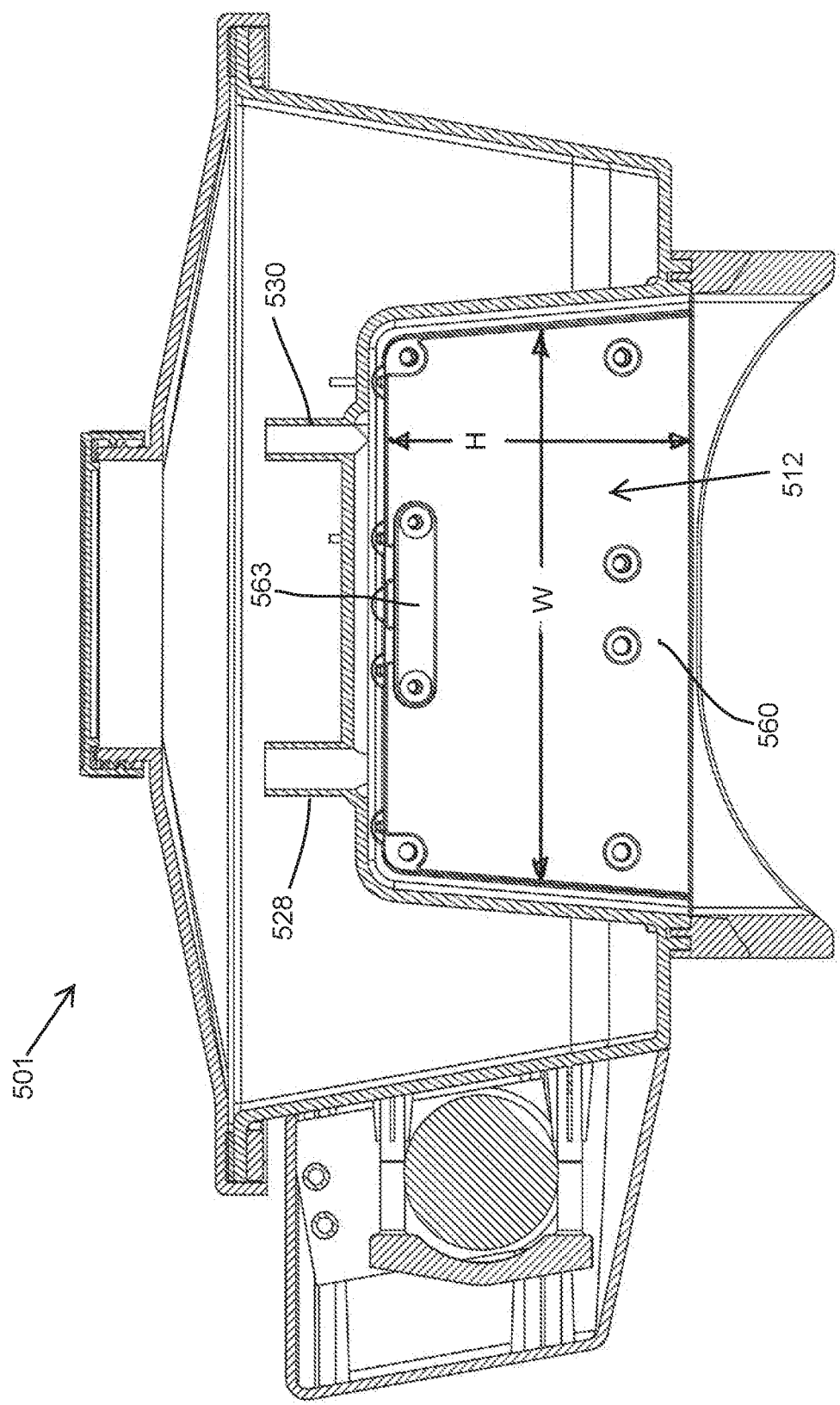
FIG. 24 shows a cross-sectional view of the applicator of FIG. 19 along the line 24.

FIG. 24 a cross-sectional view of the applicator 501 of FIG. 19 along the line 24. In this embodiment, the one cooling plate 560 may be thermally coupled to two TECs 136, however, it is within the scope of the invention to have a dedicated cooling plate for each of the TECs. It is also within the scope of the invention to have one elongated radiator thermally coupled to the two TECs along each of the side walls 518 and 520, instead of using a dedicated radiator for each of the TECs. The electrical wires 565 for the TECs 136 and the temperature sensors 563 may be routed within the chamber 512 and exit through the first pipe 528 through the tube 550 and to the power supply. The second pipe 530 may be coupled to the tube to draw air out of the chamber 512. The temperature sensors 561 may be held between the brackets 563 and the corresponding cooling plates 560 to measure the temperature of the cooling plates.

Figure 25:
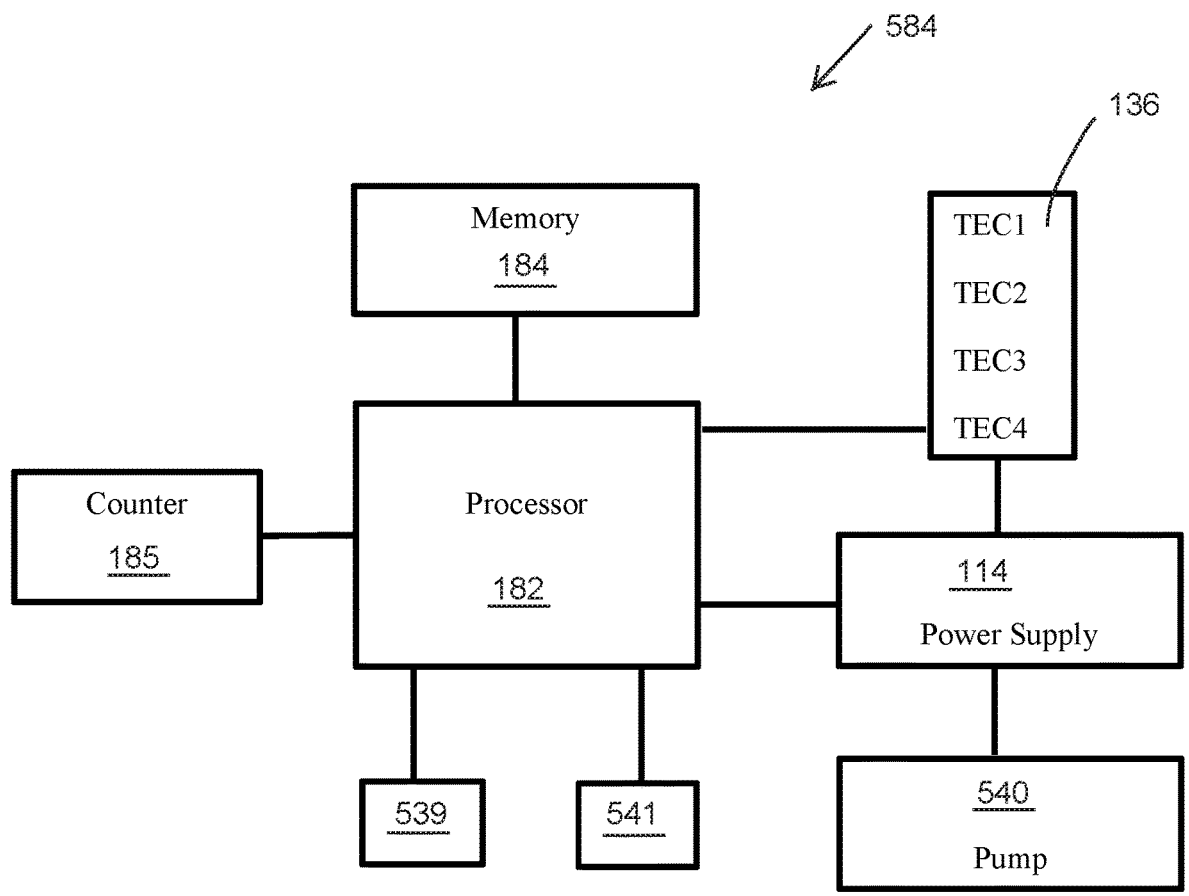
FIG. 25 shows an exemplary block diagram to operate the applicator of FIG. 19.

FIG. 25 shows a controller block diagram 584 adapted to operate the applicator 501, which is similar to the controller 180 shown in FIG. 10, with the difference being that the processor 182 controls the power supply 114 to provide power to the pump 540. The processor 182 may control the power supply 114 to adjust the voltage provide to the pump 540 to vary the speed of the pump 540, thereby adjusting the vacuum pressure within the chamber 512. The processor 182 may be communicably coupled to the power supply 114, the memory 184, one or more TECs 136, temperature sensors 561 to measure the temperature of the corresponding TECs 136 or the temperatures of the cooling plates 560, the temperature sensor 539 to measure the temperature of the coolant, and the sensor 541 to measure the coolant to determine if the coolant is an authenticate coolant or not. The processor 184 may be communicably coupled to the counter 185 configured to keep track a number of times the applicator 501 has been used.

Figure 26:
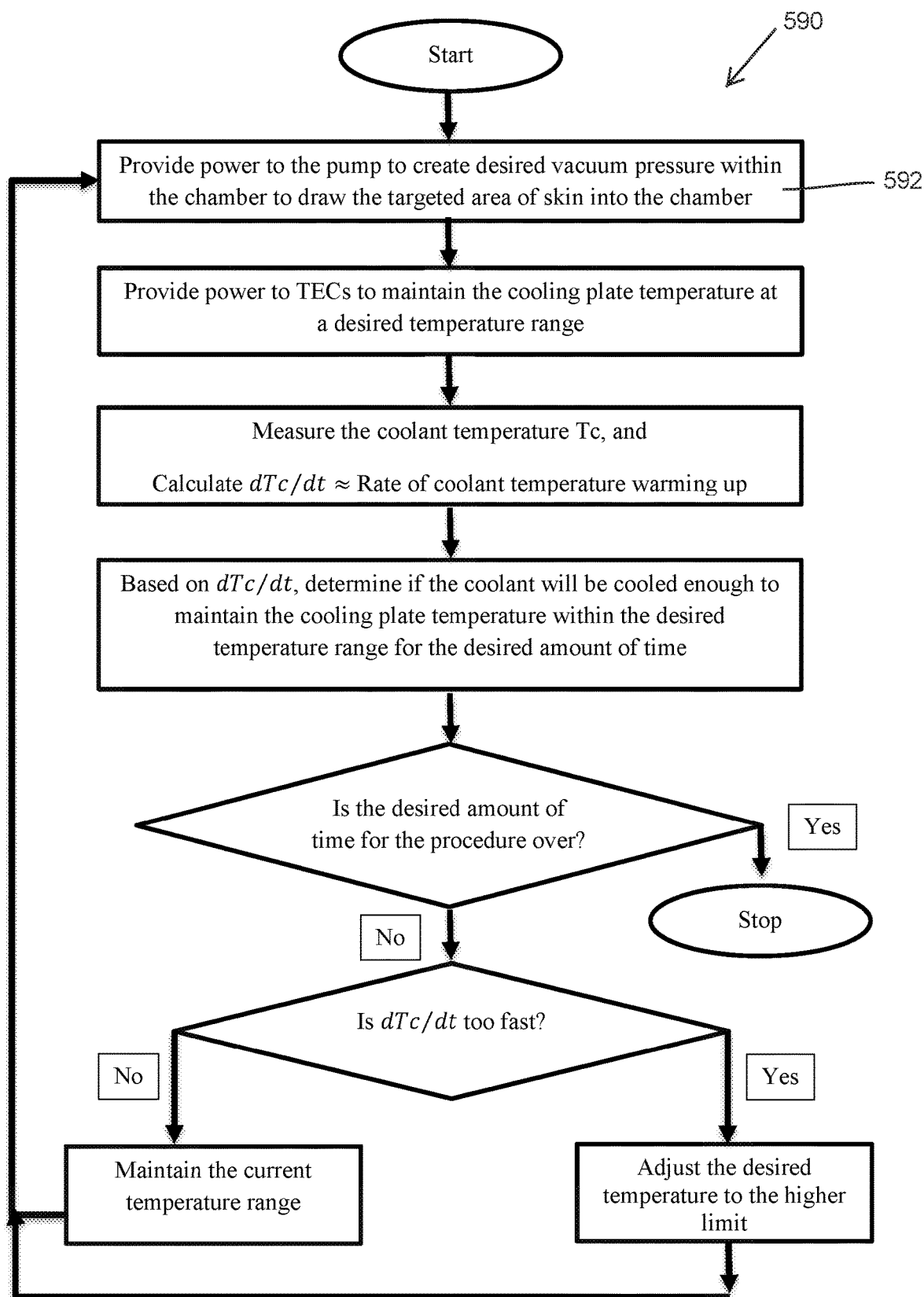
FIG. 26 shows an exemplary flow chart directed to monitoring the temperature of the coolant.

FIG. 26 shows a flow chart 590 directed to monitoring the temperature of the coolant to cool the cooling plates within a predetermined range of cooling temperature for a predetermined period of time for the applicator 501. The flow chart 590 may be similar to the flow chart 220 shown in FIG. 13 but with the addition of step 592 to provide power to the pump 540 to generate a desired vacuum pressure within the chamber 512 to draw the targeted area of the skin 570 into the chamber. The remaining steps may be substantially similar to the steps discussed in the flow chart 220. Note that other flow charts 186, 206, 240, and 270 may apply to the applicator 501, although steps in those flow charts have not been discussed relating to the applicator 501.

Testing Sample Vacuum Applicator:

For testing purposes, an applicator similar to the drawings shown in FIGS. 19 through and 24, was constructed with a container configured to hold about 112 oz of water. Four TEC1-12706 rated at 12V and 6 amp were used with each of the TECs having a square dimension of 40 mm (width)× 40 mm (height)×3.2 mm (depth). The hot side of each of the TEC was thermally coupled to a radiator which is similar to the radiator 130 described above in FIG. 8. The cold side of each of the TEC was thermally coupled to the cooling plate generally having an isosceles trapezoid shape with the W (width) of about 5.31" (135 mm) and H (height) of about 2.95" (75 mm) as shown in FIG. 24. Both the radiators 130 and the cooling plates 560 are made of aluminum material. Thermal paste were used to ensure good thermal conductivity amongst the radiators 130, TECs, and the cooling plates 560. The widths of the cooling plates and the radiators are both wider than the square opening to substantially seal around the square opening. Screws were used to couple the radiators and the cooling plates together to ensure that the radiator and the cooling plate remained in good thermal contact. Sealant was applied over the screws, and between the radiator 130 and the side walls 518 and 520 of the container, and between the cooling plates 560 and the opposite sides of the side walls 518 and 520 to substantially prevent the coolant and/or liquid from leaking out of the container.

Figure 27:
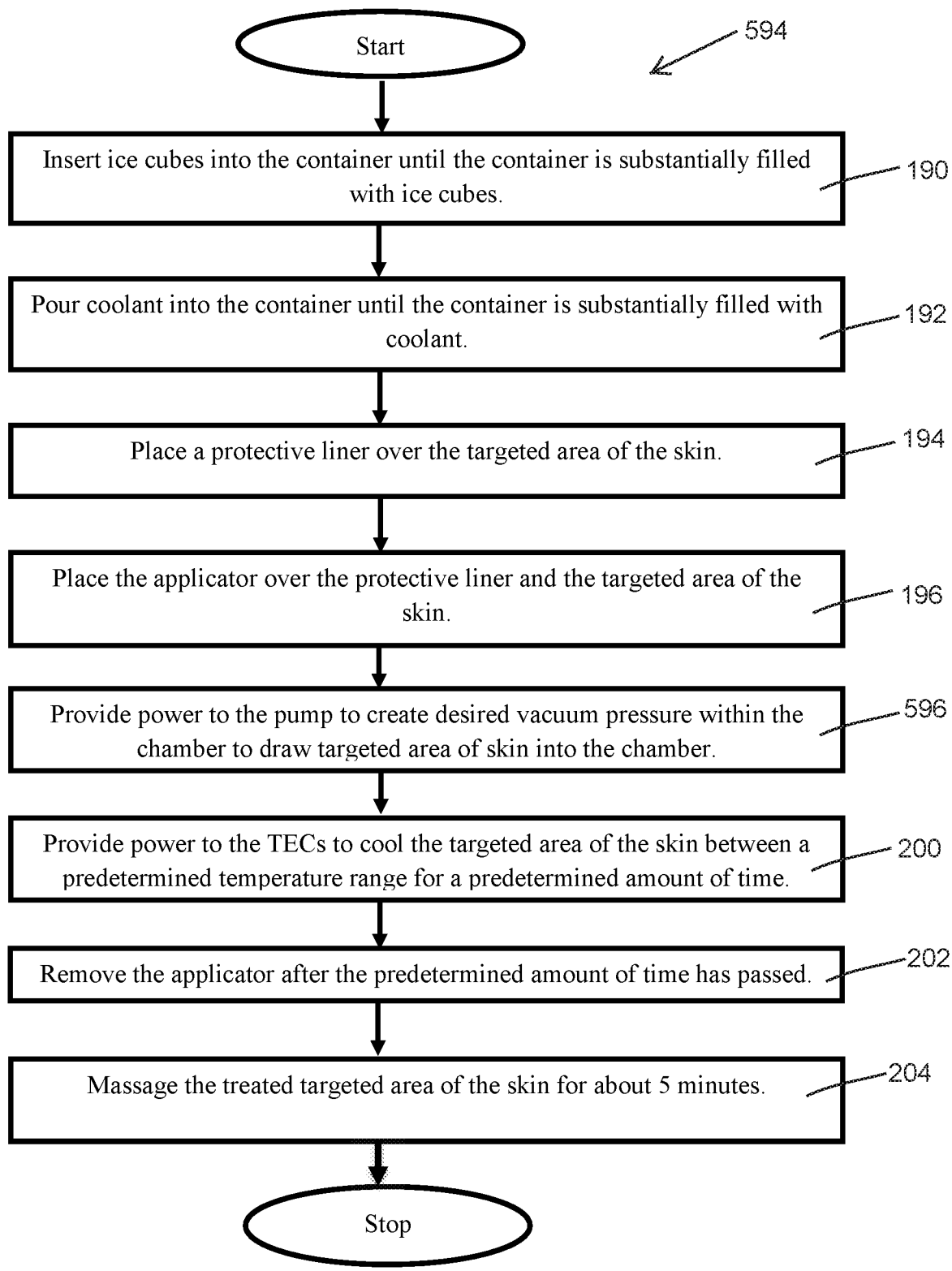
FIG. 27 shows an exemplary flow chart relating to the cooling procedure of the applicator illustrated in FIG. 19.

FIG. 27 shows a flow chart 594 relating the cooling procedure utilizing the applicator 501. The flow chart 594 may be similar to the flow chart 186 of FIG. 11, except that the step 188 may be skipped and step 596 has been added to provide power to the pump to generate a desired vacuum pressure within the chamber, as discussed in more detail. For the testing purposes, in step 190, about 1,300 grams of ice cubes (solid coolant) were inserted into the applicator 501. In step 192, the applicator 501 was then filled with about 1,600 grams of fluid coolant. The fluid coolant used in this test was formulated by using a blender to crush about 1000 grams of ice cubes with about 500 grams of chilled water at about 4° C., and about 100 grams of rubbing alcohol at about −11° C. The rubbing alcohol allowed the coolant to be more fluid so that the coolant could be poured into the container more easily. The combination of about 2900 grams or about 102 oz of ice cubes (solid coolant) and fluid coolant measured about −2° C. inside the applicator.

In step 194, a protective liner was placed over the right flank or the targeted area. In step 196, the applicator was placed over the targeted area and one thermocouples was placed between each of the cooling plates and the protective liner to measure the temperature of the both cooling plates.

In step 596, power to the pump was provided to generate a desired vacuum pressure within the chamber. The pump used for this test was from Shenzhen Yanhua Faith Technology co., ltd., a model number ZX512-903-4000 with the voltage rating of DC 9V-12V, vacuum capacity of 80 Kpa, nominal flow of 15 L/min, nominal voltage of 12V, and the power rating of 10 Watt. A variable power supply was connected to the pump and the voltage was set at about 7.0V to supply power to the pump. This caused vacuum pressure to be generated within the chamber thereby causing the targeted area of the skin to be drawn about a half way into the chamber.

In step 200, power was provided to the four TECs to cool the targeted area of the skin. Power can be provided by connecting the electrically cables to a PWM power supply to supply DC current to the four TECs. The power supply was then turned ON and OFF to further lower the temperature of the cooling plates within a temperature range of between −2° C. and −6° C. In other words, the power supply was turned ON when the temperature rose to −2° C. and it was turn OFF again when the temperature dropped to −6° C., and vice versa. The procedure lasted about 60 minutes, and at which time the power to the pump and the four TECs were turned OFF. After the procedure, some ice cubes still remained within the applicator.

In step 202, the applicator 501 was removed from the targeted area of the skin. Shortly thereafter, the temperature of the coolant was measured, and it was about 2° C. Note that after the cooling treatment, the most of the ice cubes or solid coolant have melted and mixed with the fluid coolant. The targeted area of the skin was examined, and it was noticed that some portion of the targeted area of the skin was red and protruded out somewhat like a harden butter stick, indicating that some portion of the subcutaneous fat cells were harden or crystalized. And in step 204, the targeted area of the skin was massaged to soften the hardened area of skin, and after the massage, the protruding area of the skin subsided.

After about two weeks of the cooling treatment as noted above in reference to the flow chart 594, the same targeted area of the skin, the right flank, was treated again similar to the treatment outlined in the flow chart 594. In other words, the same targeted area of the right flank was treated twice within two weeks, but the left flank was untreated to measure the difference between the treated and untreated areas of the body due to the cooling treatment outlined above. After more than 10 weeks after the second treatment on the right flank, the measurements were taken around the left and right waist circumferences from the belly button to the center back. The total waist circumference was measured to be 36.0 inches. The right side of the waist circumference, the right flank area which was treated twice, measured 17.5 inches from the center of the belly button to the center of the back. Conversely, the left side of the waist circumference, the left flank area which was untreated, measured 18.5 inches from the center of the belly button to the same center of the back so the combination of the right and left circumference measurements were same as the total waist circumference measurement of 36.0 inches. Beyond the tape measurements, the reduction of the body fat on the right flank was noticeable compared to the left flank. As such, the cooling treatments to the right flank appears to have reduced the fat cells in the treated area resulting in about 1.0″ reduction of waist circumference. Treating one side of the flank was done to eliminate the possibility that other factors may have reduced the fat cells such as either exercise or diet. Accordingly, treating both the left and right flanks may reduce the waist circumference by about 2.0 inches.

In the test conducted above, the combined initial temperature of the solid coolant and the fluid coolant in the applicator was about −2° C. With a colder combined coolant temperature in the applicator, such as below −10° C., the four TECs may cool the cooling plates to about −10° C. for about 50 minutes, at which point in time most if not all of the ice cubes in the applicator may be melted; at which time, the cooling plates may be cooled to about −5° C. for another 10 minutes. As such, depending on the duration of the cooling treatment and/or if colder temperature is desired at the cooling plates, colder fluid coolant may be utilized.

Figure 28:
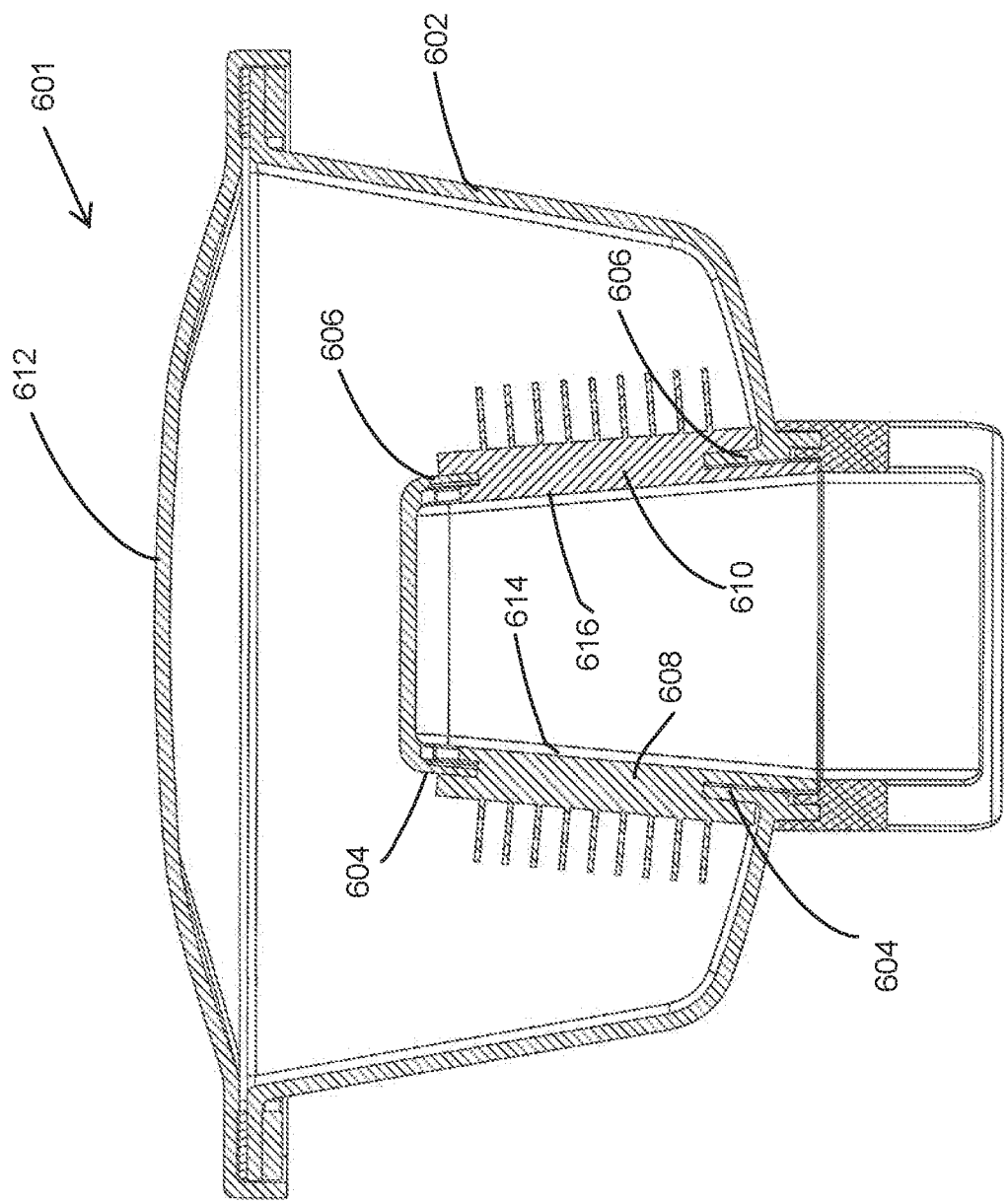
FIG. 28 shows another embodiment of a cooling system.

FIG. 28 shows an applicator 601 similar to the applicator 501 described in FIGS. 19-24 but without the cooling plate and the TEC. The applicator 601 may have a container 602 with the side walls 604 and 606 adapted to couple with radiators 608 and 610, respectively. Coolant, a mixture of solid and fluid coolants, may be inserted into the container 602 and the lid 612 may be used to seal the coolant inside the container. The applicator 601 filled with the coolant may be placed inside a freezer for a period of time to freeze the coolant and the applicator 601. The coolant may be selected such that after the applicator has been in the freezer, the coolant may remain fluid to extract the heat from the targeted area of the skin and substantially maintain the temperature along the base 614 and 616 of the radiators 608 and 610 at a desired ranged of temperature for a desired period of time.

Figure 29:
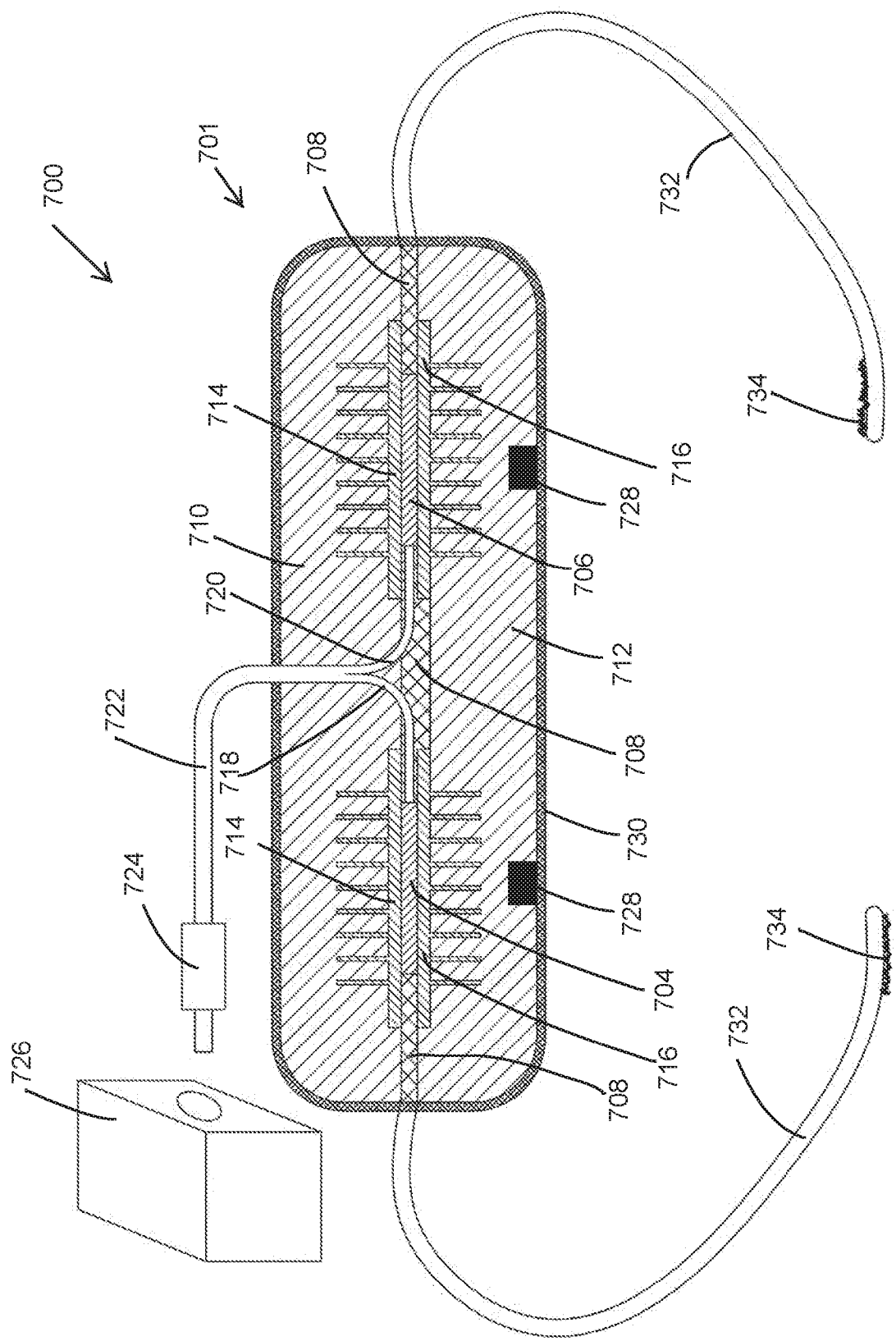
FIG. 29 shows a cross-sectional view of yet another cooling system.

FIG. 29 shows a cross-sectional view of a cooling system 700 including an applicator 701 having one or more TECs 704 and 706 coupled to an inner liner 708 dividing first and second coolants 710 and 712. The applicator 701 may be formed from flexible material so that it can conform to the contour of the targeted area of the skin. The TECs 706 may be between a first radiator 714 and a second radiator 716. Each of the TECs 704 and 706 may have wires 718 and 720, respectively, protruding from the applicator 701 to supply power to the TECs. The wires may be combined to form a cable 722 having a plug 724 adapted to plug into a power supply 726 such as a DC battery so that the cooling system 700 may be portable. The cooling system 700 may also include one or more temperature sensors 728 adapted to measure the temperature between the second compounds 712 and the targeted area of the skin. The applicator 701 may have a first side 730 adapted to make contact with the targeted area of the skin and maintain the temperature within a predetermined range of temperatures by adjusting the power supplied to the TECs 704 and 706.

The applicator 701 may be placed inside a freezer to allow the coolants 710 and 712 to reach a desired cooling temperatures such that the coolants 710 may be solid or fluid. The cooling capacity of the first and second coolants 710 and 712 may be same or different depending on the application. For instance, the coolant 712 may have a lower freezing point compared to the coolant 710, and vice versa. After the applicator 701 has been chilled, the applicator may be used for a variety of localized cryotherapy known to one skilled in the art such as for back pains, sports injuries to the knee, shoulder, ankle, elbow, and for foot injuries and for gout. The applicator 701 may include an elastic strap 732 with both distal ends 734 adapted to couple to each other such as through Velcro. Depending on the application, an antifreeze liner 160 may be placed over the targeted area of the skin to protect the skin, if the desired cooling temperature on the targeted area is too low such that it may damage the skin. Once the pouch is placed over the targeted area of the body, the temperature sensors 728 may monitor the temperature along the first side 730. If the temperature along the first side 730 is above a predetermined upper limit of cooling temperature, the power to the TECs 704 and 706 may be provided such that the cold side of the TECs cools the second radiators 716 by utilizing the first coolants 710 as the heat skin to absorb the heat from the first radiator 714.

Conversely, if the temperature sensors 728 indicate that the temperature along the first side 730 is below the predetermined cooling lower limit temperature, then the power to the TECs may be turned OFF or the polarity of the voltage may be reversed so that the first radiator 714 cools and the second radiator 716 heats. This way, by utilizing the first coolant as the heat sink, the temperature of the second coolant 712 and the first side 730 may be substantially maintained within a predetermined range of temperatures and for a longer period of time compared to traditional icepacks.

Figure 30:
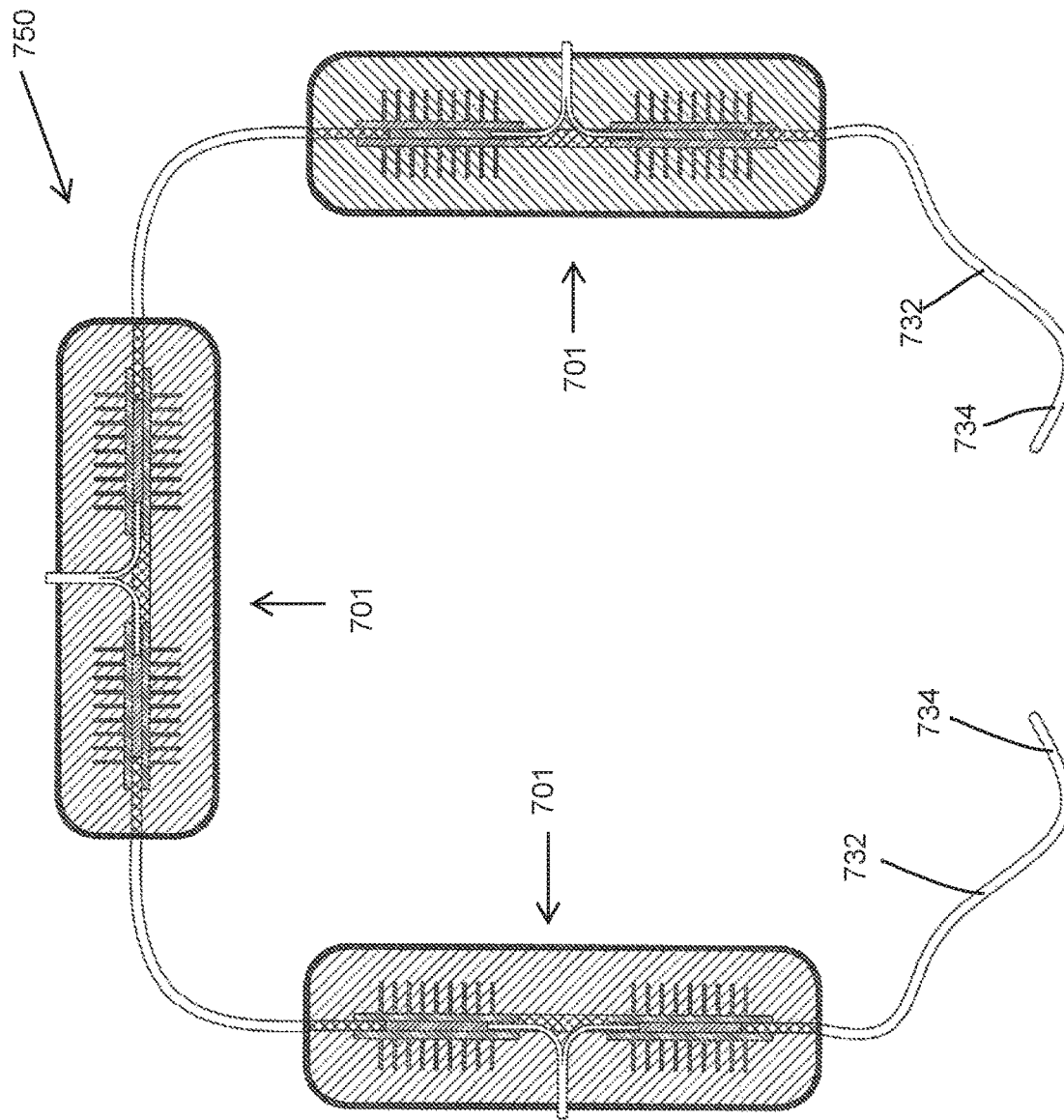
FIG. 30 show a cross-sectional view of another cooling system.

FIG. 30 show a cooling system 750 with a plurality of applicators 701 tethered together in a series with a strap 732. The cooling system 750 may be used to wrap around a larger torso area such as around the abdomen to treat the belly, and both left and right flanks at the same time.

While various embodiments of the invention have been described, it will be apparent to those of ordinary skill in the art that many more embodiments and implementations are possible within the scope of this invention. For instance, the cooling plates may formed utilizing 3D printing technology to customize certain features of the body such as chin and foot to better fit such body parts to improve the thermal conductivity between the customized cooling plate and the body parts. Moreover, various features and functionalities described in this application and Figures may be combined individually and/or plurality of features and functionalities with others. Accordingly, the invention is not to be restricted except in light of the attached claims and their equivalents.

What is claimed is:

1. A cooling system for extracting heat away from a targeted area of the body, the cooling system comprising:
   a thermoelectric cooler (TEC) having a hot side and a cold side; and
   an applicator having the TEC adapted to thermally engage with a predetermined amount of coolant such that when the TEC is powered, the predetermined amount of coolant applied to the TEC extracts heat away from the hot side of the TEC without re-cooling the predetermined amount of coolant applied to the TEC so that the cold side of the TEC can maintain temperature below 0° C. for at least 30 minutes to extract heat away from the targeted area of the body;
   wherein the cooling system does not include a pump that circulates coolant to and from the TEC.

2. The cooling system according to claim 1, wherein the applicator includes a container;
   the container has a divider that divides the container into a first section and a second section;
   the TEC is coupled to the divider;
   the first section contains the predetermined amount of coolant; and
   the second section contains a second predetermined amount of coolant such that the cold side of the TEC can extract heat away from the second predetermined amount of coolant.

3. The cooling system according to claim 1, wherein
the applicator includes a container; and
the cooling system further comprises a radiator thermally coupled to the hot side of the TEC such that, when the container is filled with the predetermined amount of coolant, the radiator is between the predetermined amount of coolant and the hot side of the TEC.

4. The cooling system according to claim 1, wherein
the applicator includes a container with a chamber; and
the cooling system further comprises a pump coupled to the chamber such that when power is provided to the pump, a predetermined vacuum pressure is generated within the chamber to draw the targeted area of the body into the chamber to allow the cold side of the TEC to extract heat away from the targeted area of the body.

5. The cooling system according to claim 1, wherein
the applicator includes a chamber, having first and second side walls, configured to draw the targeted area of the body into the chamber; and
each of the first and second side walls has at least one TEC adapted to draw heat away from the targeted area of the body.

6. The cooling system according to claim 1, further comprising:
a controller communicably coupled to the TEC to control the power provided to the TEC to maintain the temperature below 0° C. for at least 30 minutes.

7. The cooling system according to claim 1, further comprising:
a counter that is programmable with a predetermined number of authorized treatment cycles and is configured to keep track of the number of treatment cycles performed by the applicator and to deactivate the applicator after the predetermined number of authorized treatment cycles have been performed.

8. The cooling system according to claim 1, wherein
the applicator includes a container that is formed from a flexible material having a base that houses the TEC;
the cooling system further comprises a cooling plate and a radiator that can exchange heat with the predetermined amount of coolant within the container when the container is filled with the predetermined amount of coolant; and
the hot side of the TEC is thermally coupled to the radiator and the cold side of the TEC is thermally coupled to the cooling plate.

9. The cooling system according to claim 1, wherein
the predetermined amount of coolant includes solid coolant and fluid coolant; and
the fluid coolant substantially remains fluid when chilled below −5° C.

10. The cooling system according to claim 9, wherein
the solid coolant comprise ice cubes; and
the fluid coolant substantially remains fluid when chilled below −10° C.

11. The cooling system according to claim 1, wherein
the predetermined amount of coolant includes fluid coolant that substantially remains fluid when chilled below −10° C.

12. The cooling system according to claim 1, wherein
the predetermined amount of coolant is at least 60 oz and the coolant remains fluid when chilled below −10° C.

13. The cooling system according to claim 1, wherein
the applicator includes a container; and
the cooling system further comprises a cover that, when in an opened state, allows the predetermined amount of coolant to be poured into the container.

14. The cooling system according to claim 1, wherein
the applicator includes a container that is configured to hold at least 40 oz of water.

15. The cooling system according to claim 1, wherein
the applicator includes a container configured to contain the predetermined amount of coolant within the container chilled below 0° C. to allow the TEC to substantially maintain the temperature of the cold side of the TEC below 0° C. for at least 30 minutes.

16. A cooling system for extracting heat away from a targeted area of the body, the cooling system comprising:
a thermoelectric cooler (TEC) having a hot side and a cold side;
a radiator thermally coupled to the hot side of the TEC; and
an applicator having a container on which the TEC is mounted and in which the radiator is located, and the container is sized to hold a predetermined amount of coolant within the container such that, when the container is filled with the predetermined amount of coolant and the TEC is powered, the predetermined amount of coolant contained within the container extract heat away from the hot side of the TEC without re-cooling the predetermined amount of coolant contained within the container so that the cold side of the TEC can maintain temperature below 0° C. for at least 30 minutes to extract heat away from the targeted area of the body;
wherein the cooling system does not include a pumping mechanism that circulates coolant to and from the TEC.

17. The cooling system according to claim 16, wherein
the heat extracted away from the targeted area of the body crystalize at least a portion of fat cells underneath the targeted area of the skin.

18. The cooling system according to claim 16, wherein
the radiator includes a plurality of fins.

* * * * *